United States Patent [19]
Miller et al.

[11] Patent Number: 6,156,309
[45] Date of Patent: Dec. 5, 2000

[54] INSECTICIDAL COMPOSITIONS AND METHODS

[75] Inventors: Lois K. Miller, Athens, Ga.; Bruce C. Black; Peter M. Dierks, both of Yardley, Pa.; Nancy C. Fleming, Plainsboro, N.J.

[73] Assignees: University of Georgia Research Foundation, Athens, Ga.; American Cyanamid Corporation, Madison, N.J.

[21] Appl. No.: 09/228,861

[22] Filed: Jan. 12, 1999

Related U.S. Application Data

[63] Continuation-in-part of application No. 08/460,725, Jun. 2, 1995, Pat. No. 5,858,353, which is a continuation of application No. 08/281,916, Jul. 27, 1994, Pat. No. 5,662,897.

[51] Int. Cl.$^7$ .............................. A01N 63/00; C12Q 1/68; C12N 15/63; C12N 15/82; C07H 21/04
[52] U.S. Cl. .............................. 424/93.7; 424/405; 435/6; 435/320.1; 435/468; 536/23.1
[58] Field of Search .................................. 424/93.7, 405; 435/6, 320.1, 468; 536/23.1

[56] References Cited

U.S. PATENT DOCUMENTS

| | | | |
|---|---|---|---|
| 5,180,581 | 1/1993 | Miller et al. | 424/93.2 |
| 5,246,936 | 9/1993 | Treacy et al. | 514/256 |
| 5,266,317 | 11/1993 | Tomalski et al. | 424/93.2 |
| 5,352,451 | 10/1994 | Miller et al. | 424/93.2 |
| 5,858,353 | 1/1999 | Miller et al. | 424/93.6 |

FOREIGN PATENT DOCUMENTS 2005658  6/1990  Canada.

OTHER PUBLICATIONS

Crook et al. Replication, Molecular biology, and genetic engineering of granulosis viruses. Phytoparasitica. vol. 20:Suppl.,33s–38s, Jan. 1992.

Palmer et al. Genetic modification of a entomopoxvirus: deletion of the spheroidin gene does not affect virus replication in vitro. J. Gen Virol. vol. 76:15–23, Jan. 1995.

Arif, B. Recent advances in the molecular biology of entomopoxviruses. J. Gen Virol. vol. 76:1–13, Jan. 1995.

Croizier et al. (1988) "Recombination of *Autographa californica* and *Rachiplusia ou* Nuclear Polyhedrosis Viruses in *Galleria mellonella* L." *J. Gen. Virol.* 69:177–185.

Federici and Hice (1997) "Organization and Molecular Characterization of Genes in the Polyhedrin Region of the *Anagrapha falcifera* Multinucleocapsid NPV" *Arch. Virol.* 142:333–348.

Gearing and Possee (1990) "Functional Analysis of a 603 Nucleotide Open Reading Frame Upstream of the Polyhedrin Gene of *Autographa californica* Nuclear Polyhedrosis Virus" *Journal of General Virology* 71:251–262.

Kumar and Miller (1987) "Effects of Serial Passage of *Autographa californica* Nuclear Polyhedrosis Virus in Cell Culture" *Virus Research* 7:335–349.

Lee and Miller (1978) "Isolation of Genotypic Variants of *Autographa californica* Nuclear Polyhedrosis Virus" *Journal of Virology* 27:754–767.

O'Reilly and Miller (1991) "Improvement of a Baculovirus Pesticide by Deletion of the *Egt* Gene" *Bio/Technology* 9:1086–1089.

Passarelli and Miller (1993) "Three Baculovirus Genes Involved in Late and Very Late Gene Expression: *ie–l, ie–n,* and *lef–2*" *J. Virol.* 67:2149–2158.

Popham et al. (1988) "Characterization of a Variant of *Autographa californica* Nuclear Polyhedrosis Virus With a Nonfunctional ORF 603" *Biological Control* 12:223–230.

Possee et al. (1993) "Genetically Engineered Viral Insecticides: New Insecticides With Improved Phenotypes" *Pesticide Science* 39:109–115.

Possee et al. (1991) "Nucleotide Sequence of the *Autographa californica* Nuclear Polyhedrosis 9.4 kbp *Eco*RI–I and –R(Polyhedrin Gene) Region" *Virology* 185:229–241.

Vail et al. (1971) "Cross Infectivity of a Nuclear Polyhedrosis Virus Isolated from the Alfalfa Looper, *Autographa californica*" Proc. IVth Intl. Colloq. Insect Pathol., College Park, MD, pp. 297.304.

Primary Examiner—Robert A. Schwartzman
Assistant Examiner—William Sandals
Attorney, Agent, or Firm—Greenlee, Winner and Sullivan P.C.

[57] ABSTRACT

Insect viruses capable of killing at least one target insect pest quicker than previously described viruses and methods for conferring that phenotype of faster killing are provided. Further improvement in the speed of killing is obtained when the virus of this invention also contains a nonfunctional egt gene to reduce feeding by the infected larvae, inhibit growth and further mediate the earlier death of the infected insect and/or it also contains and expresses a DNA sequence encoding an insect-specific toxin. The faster killing phenotype is achieved by inactivating an ORF 603 of AcMNPV or an ORF 603 homolog of a different species of baculovirus. Improved insecticidal compositions and improved methods of controlling insects are also included within the scope of this invention.

5 Claims, 11 Drawing Sheets

```
               MluI
L-1  2469  acgcgttccggcacgagctttgattgtaataagtttttacgaagcgatga  2518
           |||||||||||||||||||||||||||||||||||||||||||||||||
V-8  2469  acgcgttccggcacgagctttgattgtaataagtttttacgaagcgatga  2518

L-1  2519  catgacccccgtagtgacaacgatcacgcccaaaagaactgccgactaca  2568
           |||||||||||||||||||||||||||||||||||||||||||||||||
V-8  2519  catgacccccgtagtgacaacgatcacgcccaaaagaactgccgactaca  2568

L-1  2569  aaattaccgagtatgtcggtgacgttaaaactattaagccatccaatcga  2618
           |||||||||||||||||||||||||||||||||||||||||||||||||
V-8  2569  aaattaccgagtatgtcggtgacgttaaaactattaagccatccaatcga  2618
                                                     *(lef-2)-->
L-1  2619  ccgttagtcgaatcaggaccgctggtgcgagaagccgcgaagtatggcga  2668
           |||||||||||||||||||||||||||||||||||||||||||||||||
V-8  2619  ccgttagtcgaatcaggaccgctggtgcgagaagccgcgaagtatggcga  2668

L-1  2669  atgcatcgtataacgtgtggagtccgctcattagagcgtcatgtttagac  2718
           |||||||||||||||||||||||||||||||| |||||||||||||||
V-8  2669  atgcatcgtataacgtgtggagtccgctcattagcgcgtcatgtttagac  2718

L-1  2719  aagaaagctacatatttaattgatcccgatgatttattgataaattgac   2768
           |||||||||||||||||||||||||||||||||||||||||||||||||
V-8  2719  aagaaagctacatatttaattgatcccgatgatttattgataaattgac   2768

L-1  2769  cctaactccatacacggtattctacaatggcggggttttggtcaaaattt  2818
           |||||||||||||||||||||||||||||||||||||||||||||||||
V-8  2769  cctaactccatacacggtattctacaatggcggggttttggtcaaaattt  2818

L-1  2819  ccggactgcgattgtacatgctgttaacggctccgcccactattaatgaa  2868
           |||||||||||||||||||||||||||||||||||||||||||||||||
V-8  2819  ccggactgcgattgtacatgctgttaacggctccgcccactattaatgaa  2868

L-1  2869  attaaaaattccaattttaaaaaacgcagcaagagaaacatttgtatgaa  2918
           |||||||||||||||||||||||||||||||||||||||||||||||||
V-8  2869  attaaaaattccaattttaaaaaacgcagcaagagaaacatttgtatgaa  2918

L-1  2919  agaatgcgtagaaggaaagaaaaatgtcgtcgacatgctgaacaacaaga  2968
           ||||||||  ||||||||||||||||||||| ||||||||||||  |||||
V-8  2919  agaatgcgcagaaggaaagaaaaatgtcgttgacatgctgaacagcaaga  2968
```

FIG.4A

```
L-1  2969  ttaatatgcctccgtgtataaaaaaaatattgaacgatttgaaagaaaac  3018
           | |||||||||||||||||||||||||||||||  ||||||||||||||||
V-8  2969  tcaatatgcctccgtgtataaaaaaaatattgggcgatttgaaagaaaac  2018
                                            $----------------

L-1  3019  aatgtaccgcgcggcggtatgtacaggaagaggtttatactaaactgtta  3068
           ||||||||| ||||||||||||||||||||||| |||||| |||||||||
V-8  3019  aatgtaccacgcggcggtatgtacaggaagagatttatattaaactgtta  3068
           --------$ L-1  3069  cattgcaaacgtggtttcgtgtgccaagtgtgaaaaccgatgtttaatca  3118
           ||||||||||||||||||||||||||||| ||||||||||||||||||||
V-8  3069  cattgcaaacgtggtttcgtgtgccaaatgtgaaaaccgatgtttaatca  3118

L-1  3119  aggctctgacgcatttctacaaccacgactccaagtgtgtgggtgaagtc  3168
           | ||||||| ||||||||||||||||||| ||||| ||||||||||||||
V-8  3119  atgctctga gcatttctacaaccacgattccaaatgtgtgggtgaagtc  3168

L-1  3169  atgcatcttttaatcaaatcccaagatgtgtataaaccaccaaactgcca  3218
           |||||||||||| |||||||||||||| || |||||||||||||||||||
V-8  3169  atgcatcttttaattaaatcccaagatgtttataaaccaccaaactgcca  3218

L-1  3219  aaaaatgaaaactgtcgacaagctctgtccgtttgctggcaactgcaagg  3268
           |||||||||| |||||||||| ||||| || |||||||||||||||||||
V-8  3219  aaaaatgaaaaatgtcgacaagctttgcccgtttgctggcaactgcaagg  3268
                                 HindIII

#(lef-2)
L-1  3269  gtctcaatcctatttgtaattattgaataataaaacaattataaatgcta  3318
           ||||||||||||||||||||||||||||||||||||||||||||||||||
V-8  3269  gtctcaatcctatttgtaattattgaataataaaacaattataaatgcta  3318

#(603 ORF)
L-1  3319  aatttgttttttattaacgatacaaaccaaacgcaacaagaacatttgta  3368
           ||||||||||||||||||||||||||||||||||||||||||||||||||
V-8  3319  aatttgttttttattaacgatacaaaccaaacgcaacaagaacatttgta  3368

MluI
L-1  3369  gtattatctataattgaaaacgcgtagttataatcgctgaggtaatattt  3418
           | ||||||||||||||||||| || ||||||||||   |||||| |||
V-8  3369  gaattatctataattgaaaacgcataattataatcgtcaaggtaatgttt  3418
```

FIG.4B

```
L-1  3419  aaaatcattttcaaatgattcacagttaatttgcgacaatataattttac  3468
            |||||||||||||||||||||||||||||||||||||| ||||||||||
V-8  3419  aaaatcattttcaaatgattcacagttaatttgcgacagtataattttgt  3468

L-1  3469  tttcacataaactagacgcct.....tgtc.gtcttcttcttcgtattcc  3512
            ||||||||||||||||||||     |||| ||| ||||||||||||||
V-8  3469  tttcacataaactagacgcctttatctgtctgtcgtcttcttcgtattct  3518

L-1  3513  ttctcttttcatttttctcctcataaaaattaacatagttattatcgta   3562
            || ||||||||||||||| ||||||||||| ||||| ||||||||||||
V-8  3519  ttttcttttcatttttctcttcataaaaattcacataattattatcgta   3568

L-1  3563  tccatatatgtatctatcgtatagagtaaattttttgttgtcataaatat  3612
            |||||||||||||| ||||| ||||||||||||||||||||| |||||||
V-8  3569  tccatatatgtatctgtcgtaaagagtaaattttttgttgtcataaatat  3618

L-1  3613  atatgtcttttttaatggggtgtatagtaccgctgcgcatagttttttctg  3662
            ||||||||||||||||||||||||||||||||||||||||||||||||
V-8  3619  atatgttttttttaatggggtgtatagtaccgctgcgcatagttttttctt  3668

L-1  3663  taatttacaacagtgctattttctggtagttcttcggagtgtgttgcttt  3712
            ||||||| | |||||||||||||||||| ||||||||||||||||||||
V-8  3669  taatttaaaccagtgctattttctggtaattcttcggagtgtgttgcttt  3718

L-1  3713  aattattaaatttatataatcaatgaatttgggatcgtcggttttgtaca  3762
            ||||||||||||||||||||||||||||||||||||||||||||||||||
V-8  3719  aattattaaatttatataatcaatgaatttgggatcgtcggttttgtaca  3768

NaeI
L-1  3763  atatgttgccggcatagtacgcagcttcttcta.................  3795
            |||||||||||||||||||||||||    ||||
V-8  3769  atatgttgccggcatagtacgcagctggctctaaatcaatatttttaaa  3818
                                                          ^^^

L-1  3796  .........gttcaattacaccatttttagcagcaccggattaacataa  3836
                    | ||||     ||||||||||| ||| ||||||||||||
V-8  3819  caacgactggatcaacattaccatttttagcaacactggattaacataa  3868

L-1  3837  ctttccaaaatgttgtacgaaccgttaaacaaaaacagttcacctcccctt  3886
            ||||||||||| |||||||| ||| ||||||||||||||||| ||
V-8  3869  ttttccaaaatgctgtacgaagcgtttaacaaaaacagttcacttccgtt  3918
```

FIG.4C

```
L-1  3887  ttctatactattgtctgcgagcagttgtttgttgttaaaaataacagcca  3936
           ||||||||||| |||||||||||||| ||||||||||||||||| ||||
V-8  3919  ttctatactatcgtctgcgagcagttgcttgttgttaaaaataacggcca  3968
```

*(603 ORF)

```
L-1  3937  ttgtaatgagacgcacaaactaatatcacaaactggaaatgtctatc...  3983
           ||||||||| |||||||||||||||| ||| |||   |||   ||||||
V-8  3969  ttgtaatgaaacgcacaaactaatattacacactaaaaaaatctatcatt  4018
```

EcoRV

```
L-1  3984  .......aatatatagttgctgatatcatggagataattaaaatgataac  4026
                  |||||||||||||||||| ||| | |||||||||||||||||
V-8  4019  tcggcttaatatatagttgctgatattatgtaaataattaaaatgataac  4068

L-1  4027  catctcgcaaataaataagtattttactgttttcgtaacagttttgtaat  4076
           ||||||||||||||||||||||||||||||||||||||||||||||||||
V-8  4069  catctcgcaaataaataagtattttactgttttcgtaacagttttgtaat  4118
```

*(polh)-->

```
L-1  4077  aaaaaaacctataaatatgccggattattcataccgtcccaccatcgggc  4126
           ||||||||||||||||||||||||||||||||||||||||||||||||||
V-8  4119  aaaaaaacctataaatatgccggattattcataccgtcccaccatcgggc  4168

L-1  4127  gtacctacgtgtacgacaacaagtactacaaaaatttaggtgccgttatc  4176
           |||||||||||||||||||||||| || |||||||||||||||||||||
V-8  4169  gtacctacgtgtacgacaacaaatattacaaaaatttaggtgccgttatc  4218
```

EspI

```
L-1  4177  aagaacgctaagc  4189
           |||||||||||||
V-8  4219  aagaacgctaagc  4231
```

FIG.4D

```
GTCGACGCGC TTCTGCGTAT AATTGCACAC TAACATGTTG CCCTTTGAAC TTGACCTCGA TTGTGTTAAT
TTTTGGCTAT AAAAAGGTCA CCCTTTAAAA TTTGTTACAT AATCAAATTA CCAGTACAGT TATTCGGTTT
           alg
GAAGCAAAAT GACTATTCTC TGCTGGCTTG CACTGCTGTC TACGCTTACT GCTGTAAATG CGGCCAATAT
EGTDEL1
─────────▶
ATTGGCCGTG TTTCCTACGC CAGCTTACAG CCACCATATA GTGTACAAAG TGTATATTGA AGCCCTTGCC
GAAAAATGTC ACAACGTTAC GGTCGTCAAG CCCAAACTGT TTGCGTATTC AACTAAAACT TATTGCGGTA
                                                              EcoRI
ATATCACGGA AATTAATGCC GACATGTCTG TTGAGCAATA CAAAAAACTA GTGGCGAATT CGGCAATGTT
TAGAAAGCGC GGAGTGGTGT CCGATACAGA CACGGTAACC GCCGCTAACT ACCTAGGCTT GATTGAAATG
TTCAAAGACC AGTTTGACAA TATCAACGTG CGCAATCTCA TTGCCAACAA CCAGACGTTT GATTTAGTCG
TCGTGGAAGC GTTTGCCGAT TATGCCGTTGG TGTTTGGTCA CTTGTACGAT CCGGCGCCCG TAATTCAAAT
CGCGCCTGCC TACGGTTTGG CGGAAAACTT TGACACGTC GGCGCCGTGG CGCGGCACCC CGTCCACCAT
CCTAACATTT GGCGCAGCAA TTTCGACGAC ACGGAGGCAA ACGTGATGAC GGAAATGCGT TTGTATAAAG
AATTTAAAAT TTTGGCCAAC ATGTCCAACG CGTTGCTCAA CAACAGTTT GGACCCAACA CACCGACAAT
TGAAAAACTA CGCAACAAGG TGCAATTGCT TTTGCTAAAC CTGCATCCCA TATTTGACAA CAACCGACCC   Δ1094 bp
GTGCCGCCCA GCGTGCAGTA TCTTGGCGGA GGAATCCATC TTGTAAAGAG CGCGCCGTTG ACCAAATTAA
GTCCGGTCAT CAACGCGCAA ATGAACAAGT CAAAAAGCGG AACGATTTAC GTAAGTTTTG GGTCGAGCAT
TGACACCAAA TCGTTTGCAA ACGAGTTTCT TTACATGTTA ATCAATACGT TCAAAACGTT GGATAATTAC
ACCATATTAT GGAAAATTGA CGACGAAGTA GTAAAAAACA TAACGTTGCC CGCCAACGTA ATCACGCAAA
ATTGGTTTAA TCAACGCGCC GTGCTGCGTC ATAAAAAAAT GGCGGCGTTT ATTACGCAAG GCGGACTACA
ATCGAGCGAC GAGGCCTTGG AAGCCGGGAT ACCCATGGTG TGTCTGCCCA TGATGGGCGA CCAGTTTTAC
CATGCGCACA AATTACAGCA ACTCGGCGTA GCCCGCGCCT TGGACACTGT TACCGTTTCC AGCGATCAAC
TACTAGTGGC GATAAACGAC GTGTTGTTTA ACGCGCCTAC CTACAAAAAA CACATGGCCG AGTTATATGC
                                       Xbal
GCTCATCAAT CATGATAAAG CAACGTTTCC GCCTCTAGAT AAAGCCATCA AATTCACAGA ACGCGTAATT
CGATATAGAC ATGACATCAG TCGTCAATTG TATTCATTAA AAACAACAGC TGCCAATGTA CCGTATTCAA
                                                          ◀─────────
                                                           EGTDEL2
                                                             taa
ATTACTACAT GTATAAATCT GTGTTTTCTA TTGTAATGAA TCACTTAACA CACTTTTAAT TACGTCAATA
AATGTTATTC ACCATTATTT ACCTGGTTTT TTTGAGAGGG GCTTTGTGCG ACTGCGCACT TCCAGCCTTT
ATAAACGCTC ACCAACCAAA GCAGGTCATT ATTGTGCCAG GACGTTCAAA GGCGAAACAT CGAAATGGAG
TCTGTTCAAA CGCGCTTATG TGCCAGTAGC AATCAATTTG CTCCGTTCAA AAAGCGCCAG CTTGCCGTGC
CGGTCGGTTC TGTGAACAGT TTGACACACA CCATCACCTC CACCACCGTC ACCAGCGTGA TTCCAAAAAA
TTATCAAGAA AAACGTCAGA AAATATGCCA CATAATATCT TCGTTGCGTA ACACGCACTT GAATTTCAAT
AAGATACAGT CTGTACATAA AAAGAAACTG CGGCATTTGC AAAATTGCT AAGAAAAAAG AACGAAATTA
TTGCCGAGTT GGTTAGAAAA CTTGAAAGTG CACAGAAGAA GACAACGCAC AGAAATATTA GTAAACCAGC
```

FIG.6A

```
TCATTGGAAA TACTTTGGAG TAGTCAGATG TGACAACACA ATTCGCACAA TTATTGGCAA CGAAAAGTTT
GTAAGGAGAC GTTTGGCCGA GCTGTGCACA TTGTACAACG CCGAGTACGT GTTTTGCCAA GCACGCGCCG
ATGGAGACAA AGATCGACAG GCACTAGCGA GTCTGCTGAC GGCGGCGTTT GGTTCGCGAG TCATAGTTTA
TGAAAATAGT CGCCGGTTCG AGTTTATAAA TCCGGACGAG ATTGCTAGTG GTAAACGTTT AATAATTAAA
CATTTGCAAG ATGAATCTCA AAGTGATATT AACGCCTATT AATTTGAAAG GTGAGGAAGA GCCCAATTGC
GTTGAGCGCA TTACCATAAT GCCATGTATT TTAATAGATA CTGAGATCTG TTTAAATGTC AGATGCCGTT
CTCCTTTTGC CAAATTCAAA GTATTGATTA TTGTAGATGG CTTTGATAGC GCTTATATTC AGGCTACCTT
TTGTAGCATT AGCGATAGTG TAACAATTGT TAACAAATCT AACGAAAAGC ATGTAACGTT TGACGGGTTT
GTAAGGCCGG ACGATGAAGG TACAACAATG CCTTATGTCA TTGGACCATT ATATTCTGTC GAC
```

FIG.6B

```
E2      TGAGACGCACAAACTAATATCACAAACTGGAAATGTCTATCA---------ATATATAG
V8      TGAAACGCACAAACTAATATTACACACTAAAAATGTCTATCATTTCGGCTTAATATATAG
V1000   TGAAACGCACAAACTAATATTACACACTAAAAAAATCTATCATTTCGGCTTAATATATAG

E2      TTGCTGATATCATGGAGATAATTAAAATGATAACCATCTCGCAAATAAATAAGTATTTTA
V8      TTGCTGATATTATGTAAATAATTAAAATGATAACCATCTCGCAAATAAATAAGTATTTTA
V1000   TTGCTGATATTATGTAAATAATTAAAATGATAACCATCTCGCAAATAAATAAGTATTTTA

E2      CTGTTTTCGTAACAGTTTTGTAATAAAAAAACCTATAAAT ATG CCG GAT TAT TCA
V8      CTGTTTTCGTAACAGTTTTGTAATAAAAAAACCTATAAAT ATG CCG GAT TAT TCA
V1000   CTGTTTTCGTAACAGTTTTGTAATAAAAAAACCTATAAAT ATG CCG GAT TAT TCA

E2      TAC CGT CCC ACC ATC GGG CGT ACC TAC GTG TAC GAC AAC AAG TAC
V8      TAC CGT CCC ACC ATC GGG CGT ACC TAC GTG TAC GAC AAC AAA TAT
V1000   TAC CGT CCG ACC ATC GGG CGT ACC TAC GTG TAC GAC AAC AAA TAT

E2      TAC AAA AAT TTA GGT GCC GTT ATC AAG AAC GCT AAG CGC AAG AAG
V8      TAC AAA AAT TTA GGT GCC GTT ATC AAG AAC GCT AAG CGC AAG AAG
V1000   TAC AAA AAC TTG GGT TCT GTT ATT AAA AAC GCC AAG CGC AAG AAG

E2      CAC TTC GCC GAA CAT GAG ATC GAA GAG GCT ACC CTC GAC CCC CTA
V8      CAC TTC GCC GAA CAT GAG ATC GAA GAG GCT ACC CTC GAC CCC CTA
V1000   CAC CTA ATC GAA CAT GAA GAA GAG GAG AAG NAC TTG GAT CCC TTA

E2      GAC AAC TAC CTA GTG GCT GAG GAT CCT TTC CTG GGA CCC GG
V8      GAC AAC TAC CTA GTG GCT GAG GAT CCT TTC CTG GGA CCC GG
V1000   GAC AAT TAC ATG GTT GCC NNA GAT CCT TTT CTA GGA CCT GG
```

FIG. 7

INSECTICIDAL COMPOSITIONS AND METHODS

CROSS REFERENCE TO RELATED APPLICATIONS

This application is a Continuation-in-Part Application of U.S. patent application Ser. No. 08/460,725, filed Jun. 2, 1995, now U.S. Pat. No. 5,858,353, which is a Continuation Application of U.S. patent application Ser. No. 08/281,916, filed Jul. 27, 1994, and issued Sep. 2, 1997, as U.S. Pat. No. 5,662,897.

ACKNOWLEDGEMENT OF FEDERAL RESEARCH SUPPORT not applicable

BACKGROUND OF THE INVENTION

The present invention relates to methods and compositions using baculoviruses for biological control of insect pests. More particularly, the present invention relates to a recombinant baculovirus which has improved properties in insect control and a genetic modification conferring improved properties, i.e., more rapid death for at least one target insect. The present invention also relates to further genetically modified baculoviruses with further improved killing properties and methods of use.

Interest in the biological control of insect pests has arisen as a result of disadvantages of conventional chemical pesticides. Chemical pesticides generally affect beneficial as well as nonbeneficial species. Insect pests tend to acquire resistance to such chemicals so that new insect pest populations can rapidly develop that are resistant to these pesticides. Furthermore, chemical residues pose environmental hazards and possible health concerns. Biological control presents an alternative means of pest control which can reduce dependence on chemical pesticides.

The primary strategies for biological control include the deployment of naturally-occurring organisms which are pathogenic to insects (entomopathogens) and the development of crops that are more resistant to insect pests. Approaches include the identification and characterization of insect genes or gene products which may serve as suitable targets for insect control agents, the identification and exploitation of previously unused microorganisms (including the modification of naturally-occurring nonpathogenic microorganisms to render them pathogenic to insects), the modification and refinement of currently used entomopathogens, and the development of genetically engineered crops which display greater resistance to insect pests.

Viruses that cause natural epizootic diseases within insect populations are among the entomopathogens which have been developed as biological pesticides. Baculoviruses are a large group of viruses which infect only arthropods (Miller, L. K. [1981] in *Genetic Engineering in the Plant Sciences*, N. Panopoulous, [ed.], Praeger Publ., New York, pp. 203–224; Carstens, [1980] *Trends in Biochemical Science* 52:107–110; Harrap and Payne [1979] in *Advances in Virus Research*, Vol. 25, Lawfer et al. [eds.], Academic Press, New York, pp. 273–355; *The Biology of Baculoviruses*, Vol. I and II, Granados and Federici [eds.], CRC Press, Boca Raton, Fla., [1986]). Baculoviruses, including *Autographa californica* nucleopolyhedrosis virus (AcMNPV), have been found in approximately 400 different species across several different insect orders; the vast majority of these viruses occur in the order Lepidoptera. Baculoviruses are known to infect insects in both natural ecosystems (e.g., forests and prairies) and monocultural agro-ecosystems (e.g., cotton fields). Many baculoviruses infect insects which are pests of commercially important agricultural and forestry crops Such baculoviruses are potentially valuable as biological control agents. Four different baculoviruses have been registered for use as insecticides by the U.S. Environmental Protection Agency.

Among the advantages of baculoviruses as biological pesticides is their host specificity. Not only do baculoviruses as a group infect only arthropods, but also individual baculovirus strains usually only infect one or a few species of insects. Thus, they pose no risk to man or the environment, and can be used without adversely affecting beneficial insect species.

Baculovirus subgroups include nuclear polyhedrosis viruses (NPV), granulosis viruses (GV), and non-occluded baculoviruses. In the occluded forms of baculoviruses (GV and NPV), the virions (enveloped nucleocapsids) are embedded in a crystalline protein matrix. This structure, referred to as an inclusion or occlusion body, is the form found extraorganismally in nature and is responsible for spreading the infection between insects. The characteristic feature of the NPVs is that many virions are embedded in each occlusion body. The NPV occlusion bodies are relatively large (up to 5 micrometers). Occlusion bodies of the GV viruses are smaller and contain a single virion each. The crystalline protein matrix of the occlusion bodies of both forms is primarily composed of a single 25,000 to 33,000 dalton polypeptide which is known as polyhedrin or granulin. Baculoviruses of the non-occluded subgroup do not produce a polyhedrin or granulin protein, and do not form occlusion bodies.

*Autographa californica* nucleopolyhedrovirus (nuclear polyhedrosis virus) (AcMNPV) is the most extensively characterized baculovirus. AcMNPV belongs to the family Baculoviridae, subfamily Eubaculovirinae, genus Nuclear Polyhedrosis Virus, and the subgenus Multiple Nucleocapsid Virus, which are characterized by the formation of viral occlusion bodies (or polyhedra) in the nuclei of infected host cells. The virus was first isolated more than 20 years ago from an alfalfa looper, *Autographa californica*, during a naturally occurring epizootic infection in California. Since then, the virus has been characterized extensively using biochemical and molecular techniques, and extensive DNA sequence within the 128 kbp genome is known. AcMNPV has been designated as the type species for the subgenus Multiple Nucleocapsid Virus.

In nature, infection is initiated when an insect ingests food contaminated with baculovirus particles, typically in the form of occlusion bodies for an NPV such as AcMNPV. The occlusion bodies dissociate under the alkaline conditions of the insect midgut, releasing individual virus particles which then invade epithelial cells lining the gut. Within a host cell, the baculovirus migrates to the nucleus where replication takes place. Initially, certain specific viral proteins are produced within the infected cell via the transcription and translation of so-called "early genes." Among other functions, these proteins are required to allow replication of the viral DNA, which begins 4 to 6 hours after the virus enters the cell. Extensive viral DNA replication proceeds up to about 24 hours post-infection (pi). From about 8 to 20 hours pi, the infected cell produces large amounts of "late viral gene products." These include components of the nucleocapsid which surrounds the viral DNA during the formation of progeny virus particles. Production of the progeny virus particles begins around 12 hours pi. Initially, progeny virus migrate to the cell membrane where they acquire an envelope as they bud out from the surface of the cell. This non-occluded virus can then infect other cells within the insect. Polyhedrin synthesis begins about 18 hours after infection and increases to very high levels by 24 hours pi. At that time, there is a decrease in the number of budded virus particles, and progeny virus are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects. Reviewed in *The Biology of Baculoviruses*, Vol. I and II, Granados and Federici (eds.), CRC Press, Boca Raton, Fla., 1986.

The ability of AcMNPV to persist and spread in the environment is governed by many interrelated factors (reviewed by Evans, H. [1986] *The Biology of Baculoviruses, Ecology and Epizoology of Baculoviruses*, Granados, R. R. and Federici, B. A. [eds.] pp. 89–132). Factors such as the relative sensitivity of the insect host to virus, as well as developmentally determined sensitivity to AcMNPV, are important. Host density also appears to play an important role in determining persistence and spread of baculoviruses. There are important implications concerning the role of biotic and abiotic forces that determine AcMNPV environmental transmission and persistence. For example, predators compete with virus for available insect hosts and tend to reduce potential virus productivity by removal of these virus-susceptible hosts from the environment. On the other hand, predators can also indirectly increase the survival capacity and spread of MNPVs by increasing virus dispersal and by making more efficient use of available host populations. This predator-aided transmission is generally by passage of infectious MNPVs through the gut of predatory insects, birds, and mammals. Likewise, abiotic factors (such as ultraviolet (UV) light, rainfall, temperature, and pH) have a major influence on virus survival and spread in the environment. For example, baculoviruses appear to be particularly sensitive to UV irradiation and to alkaline pH. Persistence of field applied virus without UV protection can be as little as 1–2 days in the field. Soil appears to be a particularly important reservoir for persistence of baculoviruses. The decline of viruses in the soil is slow and wide range of times for persistence and viability have been reported. The ubiquitous and harmless association between baculoviruses and humans and other species due to dietary exposure underscores their safety and value as insecticides.

One potential disadvantage to using baculoviruses as pesticides has been the length of time between virus ingestion and insect death. During this time, the pest insect continues to feed and damage crops. Because pesticides are generally applied only after an infestation is apparent, it is critical that the time of feeding be minimized. One approach to lessening insect feeding time in insect control via viral infection is the use of ecdysteroid glycosyl transferase-deficient baculovirus (O'Reilly and Miller [1991] *Biotechnology* 9:1086–1089; U.S. Pat. No. 5,180,581, Miller and O'Reilly; U.S. Pat. No. 5,352,451, issued Oct. 4, 1994, all of which are incorporated by reference). Other approaches include the insertion of genes encoding insect toxins or hormones into the viral genome (Hammock et al. [1993] *Arch. Insect Biochem. Physiol.* 22:315–344; McCutchen et al. [1991] *Bio/Technology* 9:848–852; Tomalski and Miller (1991) *Nature* 352:82–85; Stewart et al. [1991] *Nature* 352:85–88); U.S. Pat. No. 5,266,317, issued Nov. 30, 1993, Tomalski and Miller, which discloses insect-predacious mite toxins; Canadian Patent Application 2,005,658, Zlotkin et al.; Zlotkin et al. [1971] *Toxin* 9:1–8, which disclose *Androctonus australis* toxin sequences, Chejanovsky et al. (1995) *FEBS Lett.* 376:181–184, scorpion toxin; Prikhod'ko et al. [1996] *Biol. Control* 7:236–244; Hughes et al. [1997] *J. Invert. Pathol.* 69:112–118, spider toxins).

There is a need for biological pesticides, specifically insect viruses, which reduce feeding by the insect before death and/or which result in a shorter time between infection and death when compared to prior art insect viruses. A biological pesticide is preferred because it creates less of an environmental hazard than a chemical pesticide. Methods for improvement of naturally occurring viral pesticides are of further urgent need in the art.

SUMMARY OF THE INVENTION

This invention specifically provides a method for the genetic modification of a baculovirus to produce one which has improved killing properties as compared with prior art baculoviruses against at least one insect pest. This is accomplished by inactivating an ORF 603 or ORF 603 homolog in a baculovirus genome. As specifically exemplified, the inactivation of the ORF 603 of AcMNPV produces a baculovirus derivative which is improved over the wild-type comparison AcMNPV. Improved killing properties means that when at least one species of insect pest is infected, the time between infection and insect death is shorter than with a comparison AcMNPV, e.g., AcMNPV E2 (ATCC VR-1344) or AcMNPV L-1.

A further specific object of the present invention is an ORF 603-deficient (or ORF 603 homolog-deficient) baculovirus derivative which has been further genetically engineered to inactivate the gene encoding ecdysteroid glycosyltransferase (egt). One such embodiment is V8vEGTDEL, which is the AcMNPV V-8 derivative in which a portion of egt is deleted, with the result that a functional ecdysteroid glucosyltransferase is not produced during the viral infection process.

The present invention provides methods for improving the killing properties of a baculovirus by inactivating an ORF 603 or a homolog thereof to produce a phenotype of improved killing, e.g., faster insect death of at least one species of insect pest after infection, e.g., and by confirming the improved killing property by determining that the $LT_{50}$ (time required for killing 50% of test larvae at a standard virus dose, using a dose killing 90% of test larvae by set time post infection) is shorter for the genetically engineered strain than for the parental baculovirus. The genetically engineered strain may be produced by molecular biological techniques using an insect virus selected from the group consisting of nuclear polyhedrosis viruses including, but not limited to, *Anagrapha falcifera* NPV (AfNPV), *Rachiplusia ou* NPV, *Lymantria dispar* NPV, *Autographa californica* NPV, *Synographa falcifera* NPV, *Spodoptera lituralis* NPV, *Spodoptera exigua* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV and *Manduca sexta* NPV; granulosis viruses including, but not limited to, *Cydia pomonella* GV, *Pieris brassicae* GV and *Trichoplusia ni* GV. Non-occluded viruses similar to the baculoviruses may also be genetically modified to improve their killing properties for particular target insects; examples of such non-occluded viruses include, but are not limited to, *Oryctes rhinoceros* and *Heliothis zea* non-occluded insect viruses. Inactivation of sequences functionally equivalent to the AcMNPV ORF 603 confer improved killing properties in viruses other than as specifically exemplified herein.

Further objects of the present invention are insecticidal compositions comprising the baculoviruses with improved killing properties against at least one insect pest, wherein the improved killing properties are the result of genetically modifying the baculovirus to inactivate an ORF 603 or ORF 603 homolog. Preferred viruses include AcMPNV 603-deficient derivatives, AfNPV ORF633-deficient derivatives, and nuclear polyhedrosis viruses and granulosis viruses and non-occluded baculoviruses genetically modified to inactivate ORF 603 or an ORF 603 homolog in a non-limiting fashion. Insecticidal compositions of the present invention can be formulated as wettable powders or any other formulation known to the art useful for agricultural and/or environmental use. An exemplary composition of a wettable powder insecticidal composition is as follows:

| Ingredient | Nominal Percent (w/w) |
|---|---|
| V8vEGTDEL polyhedrin inclusion bodies | 10.0% |
| MORWET D425 | 30.0% |
| MOREWET EFW | 20.0% |
| Kaolin Clay | 16.0% |
| MICROCEL E | 16.0% |
| UV-9 oxybenzone or charcoal | 5.0% |
| EUDRAGIT S100 | 2.0% |
| Citric Acid | 0.9% |
| polyethylene glycol MW400 | 0.1% |

Optionally, a stilbene brightener can be added to the formulation to enhance infectivity or potentiate the insecticidal effects of the insect virus.

An insecticidal composition of the present invention can be formulated, for example, as follows: preparing an aqueous suspension of EUDRAGIT S100 (1% w/v); dissolving the EUDRAGIT S100 by adjusting the pH of the suspension to 9.0 to 9.5; adding viral PIBs and UV-9 oxybenzone or charcoal to the previous solution, and blending to produce an even suspension; air drying the even suspension; milling the dried material to produce milled material; and dry blending the milled material with MORWET D425, MOREWET EFW wetting agent, Kaolin Clay as a bulking agent, MICROCEL E as a flow agent, citric acid and polyethylene glycol MW400 to provide flexibility to the milled material. Other insecticidal virus-compatible formulations may be substituted for the foregoing.

BRIEF DESCRIPTION OF THE DRAWINGS

FIG. 3A is the map for the AcMNPV L-1 wild type (thin line represents L-1 DNA). FIG. 3B is the map of AcMNPV V-8 (thick line represents V-8 DNA). The extra HindIII site in lef-2 is one distinguishing (physical) characteristic of V-8. V-8 is missing both the MluI site within the 603 ORF and the EcoRV site between the 603 ORF and polh. The V-8 603 ORF has a premature stop codon generated by an insertion and is predicted to produce an incomplete, non-functional polypeptide product (note "X" through the 603 ORF). FIG. 3C is the map of vEcoRIHybI recombinant virus containing the portion of the V-8 genome indicated by the thick bar. Although the transfer plasmid used to construct this hybrid contained V-8 sequence to the MluI site at 1.93 m.u., allelic replacement limited V-8 sequences to the portion of lef-2 indicated. FIG. 3D is the map of vEcoRIHybIFS recombinant virus containing the entire V-8 MluI (1.93 m.u.) to EspI (3.27 m.u.) fragment. The NaeI site in what was the 603 ORF has been destroyed via a four base pair deletion (asterisk denotes missing NaeI site).

FIGS. 4A–4D present the DNA sequence of AcMNPV L-1 (SEQ ID NO:1) from the 327 ORF MluI site (nucleotide 2469) to the polh EspI site (nucleotide 4186) aligned with the corresponding sequence from the AcMNPV V-8 variant (SEQ ID NO:3). The deduced amino acid sequences of the LEF-2 proteins are given in SEQ ID NO:2 and 4. The V-8 sequence has a multitude of point mutations and four insertions as compared to the L-1 sequence. Identities are indicated by a vertical line. Sequence differences and insertions are in bold type. Start-points of lef-2, the 603 ORF and polh are marked with asterisks (*). The natural termination codons of the L-1 lef-2 and 603 ORF are marked with pound signs. Crossover in vEcoRIHybI occurred in the dashed region between the two dollar signs at nucleotides 3003 and 3027. The premature stop codon generated by the insertion in the V-8 603 ORF is indicated by three consecutive carets. Sequence numbering in parentheses corresponds to that in O'Reilly et al. (1992) Baculovirus Expression Vectors: A Laboratory Manual, W. H. Freeman & Co., N.Y.

FIGS. 6A–6B present the nucleotide sequence of AcMNPV DNA in the region of the egt gene (SEQ ID NO:5). The codons for translation initiation (atg) and termination (taa) for the egt open reading frame are indicated over the sequence. The 1094 bp fragment deleted in the EGTDEL virus is underlined. The positions from which the oligonucleotide primers (EGTDEL1 and EGTDEL2) used for PCR amplification are shown.

FIG. 7 presents DNA sequences for AcMNPV E2 (SEQ ID NO:6), AcMNPV V-8 (SEQ ID NO:7) and V1000 (SEQ ID NO:8) virus strains beginning at the Esp31 site upstream of the polyhedrin gene and extending into the polyhedrin coding region. The sequences were from one strand using primer PV1 Reverse, and nucleotides indicated as N were not identified.

DETAILED DESCRIPTION OF THE INVENTION

Figure 1A:
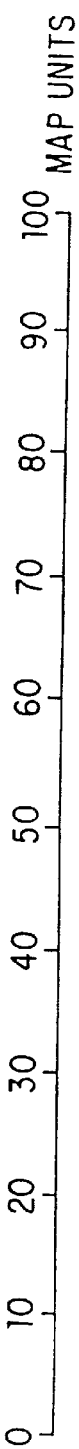
FIGS. 1A–C present a schematic representation of the AcMNPV genome showing the location of the egt and genes. The AcMNPV genome is presented in map units and as EcoRI and HindIII restriction maps.

Because faster acting insect viruses are desirable as insect control agents, a study was undertaken to search for baculovirus strains with such improved killing properties. Toward this end, a minimally passaged (in insect larvae) AcMNPV virus stock was amplified, plated in culture to obtain clonal isolates, and these isolates were examined for restriction site polymorphisms and for increased virulence in insect larvae. A minimally passaged stock was used as the starting material for this survey, in part because serial passage in cell culture was known to lead to mutations and perhaps reductions in virulence in AcMNPV (see, e.g., Kumar and Miller [1987] *Virus Research* 7:335–349). Genotypic variants of AcMNPV were known (Lee and Miller [1978] *J. Virol.* 27:754–767). AcMNPV was the baculovirus for which a more virulent (i.e., faster killing) variant was sought because it is known to infect a relatively large number of insect pests of particular economic importance in agriculture.

The AcMNPV V-8 isolate was one of ten viral clones plaque purified on SF-21 cell monolayers inoculated with diluted hemolymph from *Heliothis virescens* larvae that had been orally infected with a minimal passage stock of the original Vail AcMNPV isolate (Vail et al., [1971] *Proc. IV Int. Collog. Insect Pathology*, College Park, Md. pp. 297–304). All ten viral isolates, V-1 through V-10, were initially characterized by restriction endonuclease analysis with BamHI, BglII, EcoRI, HindIII, PstI, and XhoI and compared to AcMNPV L-1. The pattern of V-10 is identical to that of L-1. The profiles of V-1, V-2, V-3, V-6, V-7, V-8 and V-9 all approximately 8.5 kb of HindIII-F fragment and instead contain two novel fragments of approximately 7.4 kb and 1.1 kb. Two isolates, V-4 and V-5, have a restriction pattern intermediate between the first two viral types (containing submolar quantities of the HindIII-F fragment and both the novel fragments of 7.4 kb and 1.1 kb). The presence of submolar fragments suggests that V-4 and V-5 are incompletely purified viral stocks, as all samples were plaque purified only once to preserve the virulence of the isolates. No differences in restriction profiles were detected between any of these ten clones and L-1 using BamHI, BglII, EcoRI, PstI, and XhoI digestion.

The V-8 isolate of AcMNPV was selected as representative of the predominant genotype of the ten isolates and was further characterized using *Spodoptera frugiperda* neonate bioassays. Data from representative bioassays evaluating oral infectivity ($LC_{50}$) and virulence ($LT_{50}$) are presented in Table 1. $LC_{50}$ is the amount of virus at which 50% of infected larvae are dead within ten days after infection. $LT_{50}$ is the time after infection when 50% of the infected larvae are dead when exposed to virus at $LC_{90}$ unless otherwise indicated hereinbelow. In *S. frugiperda* and *Trichoplusia ni* neonates, the $LC_{50}$s of the L-1 and V-8 AcMNPV strains are very similar, but the $LT_{50}$s are significantly different in *S. frugiperda* neonates. For AcMNPV strains E-2 and L-1, death from infection normally occurs at about the same time after infection while V-8 causes death more quickly post infection than the L-1 and E2 strains. There is variability in the actual time until death from experiment to experiment, but the results are consistent from experiment to experiment for comparisons of the percent difference in time until death in the V-8 versus L-1 or E-2 comparisons. The average $LT_{50}$ at $LC_{90}$ of the V-8 isolate in *S. frugiperda* neonates is consistently about 12% shorter than the average $LT_{50}$ of L-1.

Initial restriction analysis of AcMNPV V-8 versus AcMNPV L-1 with a battery of different restriction endonucleases (BamHI, BglII, EcoRI, HindIII, PstI, and XhoI) showed only the HindIII restriction polymorphism discussed above. The six restriction endonucleases used to characterize AcMNPV V-8 recognize a total of 95 sites in the AcMNPV genome, counting each EcoRI hr region (six short regions with highly repetitive DNA sequences and multiple EcoRI sites) as one site. Since each recognition site is a hexanucleotide, a total of 570 bp have been screened for mutations by restriction endonuclease analysis. The only difference found in this screen was a HindIII restriction polymorphism in lef-2 (a 0.18% mutation rate 1/570). The V-8 strain was subsequently shown to lack the EcoRV site which is located at about 90 bp upstream of the polyhedrin translation start site (see, e.g., FIGS. 6A–6B).

Figures 2A, 2B:
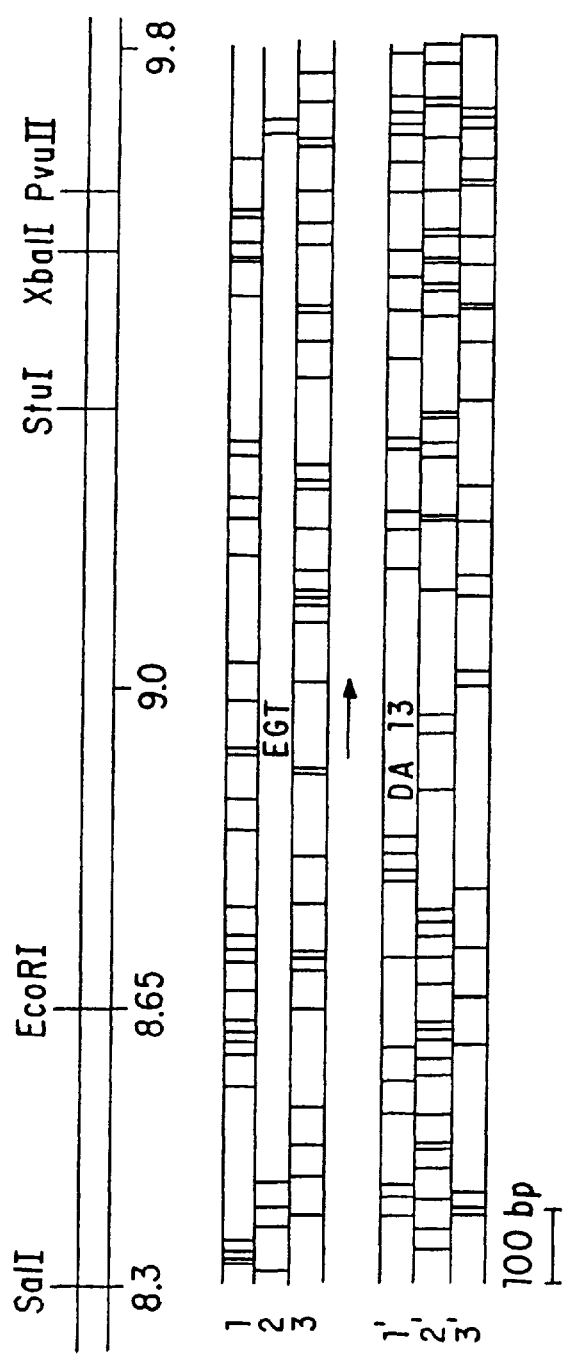
FIG. 2A is a schematic representation of the structures of the egt gene region of AcMNPV with restriction sites.
FIG. 2B shows the location of the egt gene.
Figure 3A:
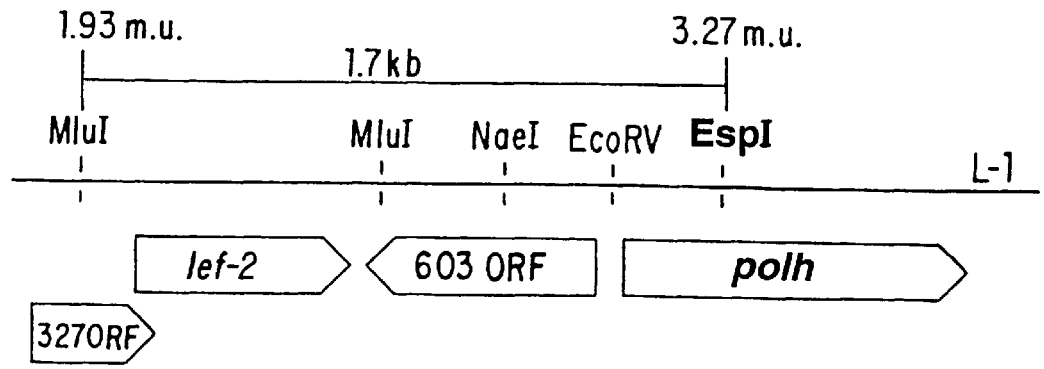
FIGS. 3A–3D represents partial restriction maps of the 327 ORF, lef-2, the 603 ORF, and the polyhedrin gene (polh) region of AcMNPV strains.
Figure 3B:
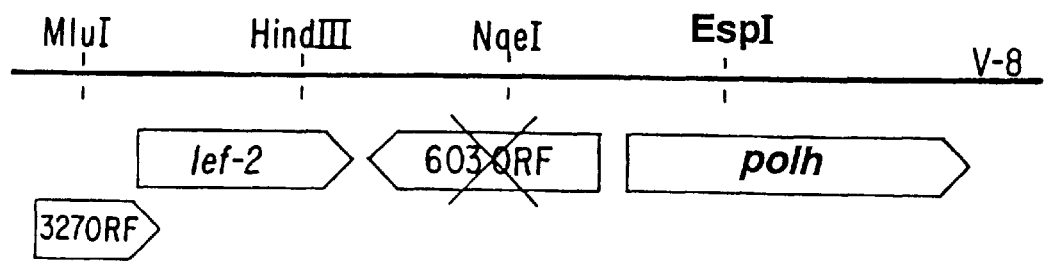
Figure 3C:
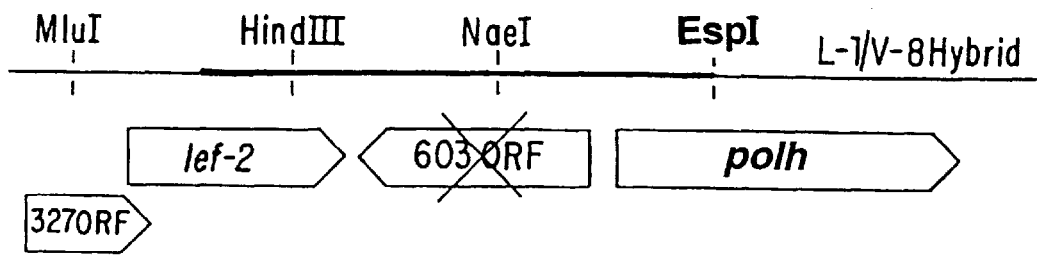
Figure 3D:
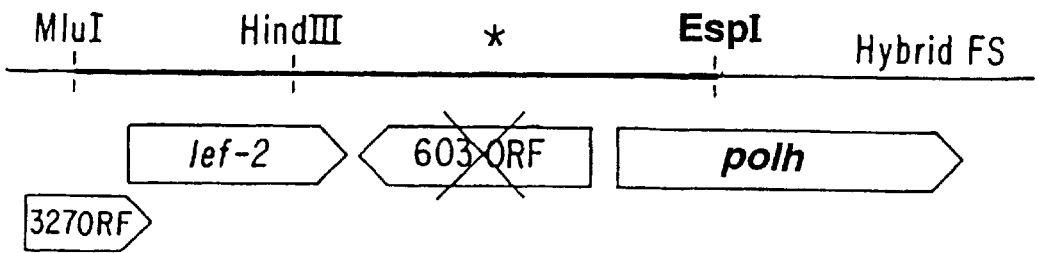

Sequence analysis of 1.72 kb in the region surrounding the HindIII polymorphism revealed numerous nucleotide differences between L-1 and V-8 sequences in and around lef-2, the 603 ORF, and the polyhedrin gene (polh) (9.3 map units (m.u.) to 3.27 m.u.) (FIGS. 2A–2B). There are 73 nucleotide changes in the 1.72 kb sequenced region. The HindIII restriction polymorphism in V-8 is due to a C to T mutation at nucleotide 3243. Both the MluI site (3389) in the 603 ORF and the EcoRV site (4001) between the polyhedrin gene and the 603 ORF were destroyed by single nucleotide changes (Table 7). Several nucleotide substitutions in this region result in amino acid sequence changes in the predicted polypeptide products of lef-2, while insertions and substitutions substantially alter the 603 ORF. The six predicted amino acid changes in lef-2 are shown in Table 7. A 26 bp insert in the 603 ORF creates a stop codon within the open reading frame of the 603 ORF and is predicted to cause premature termination during 603 ORF translation. No sequence differences were discovered in the 327 ORF as far upstream as the MluI site. Only three DNA sequence differences between V-8 and L-1 were discovered in polh. These are third base pair changes which do not change the encoded amino acids. The region about 90 bp upstream of the polyhedrin translation start site of polh was generally unchanged, although the EcoRV site present in L-1 is absent in V-8.

Therefore, based on sequence and restriction analysis, this region of V-8 contains an unusually high density of mutations using L-1 as a wild-type comparison. Without wishing to be bound by any particular theory, it is postulated that AcMNPV V-8 arose by recombination between AcMNPV and a virus relatively distantly related to AcMNPV. Furthermore, considering the mutation density of V-8 in this region, the differences at nucleotides 2703 and 4194 of V-8 (FIG. 4) may be the limits of the recombination, as no sequence differences were found as far downstream of the BamHI site in polh and as far upstream as the 327 ORF MluI site (beginning at nucleotide 1 in SEQ ID NO:3) at nucleotide 2469 (FIG. 2). Most of the mutations are concentrated in the 603 ORF and, to a lesser extent, in lef-2. Furthermore, complete V-8 vs. L-1 sequence analysis of the relatively distant 504 ORF (a phosphatase gene located between 0.0 m.u. and 0.4 m.u.) revealed no differences between L-1 and V-8.

The *H. virescens* colony at the American Cyanamid Agricultural Research Center, Princeton, N.J., was derived from a field isolate (Stoneville, Miss.) in 1966, and has been maintained since 1966. Air, water and diet are not thoroughly sterilized before coming in contact with *H. virescens*. It has been discovered that there are sporadic viral outbreaks in this colony. Virus, termed V1000, has been isolated from this colony, partial genomic DNA sequence has been determined and various properties of the virus have been characterized. The V1000 Nuclear Polyhedrosis Virus appears to be most closely related to *Rachiplusia ou* Nuclear Polyhedrosis Virus (RoNPV) based on restriction endonuclease analysis.

Based on a sequence comparison of V-8 and V1000 polyhedrin regions, but without wishing to be bound by any particular theory, it is postulated that AcMNPV strain V-8 is a recombinant between AcMNPV and the V1000 virus. A comparison of sequence between AcMNPV E-2 (ATCC VR-1344, American Type Culture Collection, 10801 University Blvd, Manassas, Va.), V1000 and AcMNPV V-8 (ATCC VR-2465) is presented in FIGS. 6A–6B. The last sequence difference between the AcMNPV V-8 and E-2 strains occurs at the twentieth codon of the polyhedrin coding sequence.

Two recombinant viruses, vEcoRIhybI and vEcoRIHybIFS, were constructed by allelic replacement (see Example 3 and FIGS. 2A–2B) to determine if the reduced $LT_{50}$ of AcMNPV V-8 was correlated with the sequence differences observed in the lef-2 region. Sequence analysis established which V-8 characteristic sequence differences these recombinants possessed following allelic recombination. Both recombinants had recombined downstream of the KpnI site in polh as evidenced by their occlusion positive phenotype. The parent virus vSynVI$^-$gal lacks polh sequences upstream of the KpnI site. The virus vEcoRIHybIFS contained the entire 1.72 kb MluI to EspI (1.93–3.27 m.u.) fragment with a four bp deletion at the NaeI site in what was the 603 ORF. The deletion in the V-8 603 ORF was intended to destroy the function of the product of the 603 ORF, but subsequent sequence analysis revealed that the V-8 603 ORF was already disrupted. Thus, this deletion is expected to have no additional effect on viral infectivity and virulence. Crossover during the allelic replacement event generating VEcoRIHybI occurred at some point between nucleotides 3003 and 3027 of AcMNPV sequence in FIGS. 4A–4D (between nucleotides 535 and 559 of SEQ ID NO:3; FIGS. 4A–4D and 6A–6B) and before the KpnI site within the polyhedrin gene. Thus, the lef-2 gene product of VEcoRIHybI is predicted to be a hybrid containing L-1-like amino acid residues upstream of the crossover and V-8-like residues downstream of the crossover (FIGS. 4A–4D and 6A–6B).

Bioassays to determine infectivity and virulence of the viruses L-1, V-8, VEcoRIHybI, and VEcoRIHybIFs were performed on *Spodoptera frugiperda* neonates. Both $LC_{50}$s and $LT_{50}$s were computed using probit analysis (Daum [1970] *Bulletin of the Entomological Society of America* 16:10–15) for each virus (Table 1). The $LC_{50}$s of all four viruses were statistically equivalent. As previously noted, V-8 has a 12.4% shorter $LT_{50}$ at $LC_{90}$ than L-1, reflecting increased virulence. The differences between the $LT_{50}$s at $LC_{90}$ of V-8, vEcoRIHybI and vEcoRIHybIFs are not statistically significant. However, the differences between the $LT_{50}$s at $LC_{90}$ of L-1 and each of the three viruses containing V-8 DNA are statistically significant; V-8 and the two hybrid viruses each had a significantly shorter $LT_{50}$ than L-1. Hybrid virus vEcoRIHybI contains only a small region of the V-8 sequences from the middle of lef-2 to the 5' end of polh but possesses the increased virulence characteristic of V-8. That the lef-2 gene product of vEcoRIHybI has an L-1-like amino-terminus and a V-8 carboxy-terminus but still retains the V-8 virulence phenotype indicates that the increased virulence (decreased $LT_{50}$) of V-8 is due to the absence of a functional 603 ORF gene product.

Gearing and Possee (1990) *J. Gen. Virol.* 71:251–262 determined that the 603 ORF is not essential for production of budded virus in cell culture, production of polyhedra, or the infectivity ($LC_{50}$) of AcMNPV, and no data relevant to the virulence as measured by $LT_{50}$ of their 603 ORF deletion mutant were presented. Passarelli and Miller (1993) *J. Virol.* 67:2149–2158 reported that lef-2 and its 630 amino acid expression product is required for late and very late gene expression in transient expression assays.

As used herein, ORF 603 is the term given to the 603 bp open reading frame from AcMNPV as given in SEQ ID NO:9, nucleotides 1-603. As specifically exemplified, the 603 ORF is from the L-1 strain of AcMNPV. The corresponding sequence of AcMNPV C6 is given in Gearing and Possee (1990) *J. Gen. Virol.* 71:3251–262. In the context of the present invention, a 603 ORF homolog is a baculovirus encoded protein of about 170–250 amino acids which has at least 75% amino acid sequence identity with the exemplified sequence, preferably at least 80%, greater than 85%, or more than 90% sequence identity. In calculations of percent identity, gaps introduced into either the AcMNPV ORF603 reference sequence or the comparison sequence to optimize alignment are treated as mismatches. The number of comparison sequence matches divided by the 201 (amino acids in AcMNPV ORF603) times 100% gives percent sequence identity. Any of a number of commercially and publicly available sequence comparison computer programs can be used (PILEUP, BLAST, CLUSTAL, among others). A functional 603 ORF homolog is one which is an open reading frame and encodes a functional protein. A specifically exemplified ORF603 homolog is the ORF633 of AFNPV [See Federici and Hice (1997) *Arch. Virol.* 142:333–348]. The function of the 603 ORF of AcMNPV is not known, but it is not a gene essential for infection or viral replication (Gearing and Possee [1990] supra). When a 603 ORF homolog in a baculovirus is inactivated, that baculovirus derivative has increased virulence, as measured by decrease in the time required to kill an infected insect larva as compared to the time required to kill an infected larvae by the isogenic baculovirus having a functional 603 ORF or ORF 603 homolog.

TABLE 1A

Bioassays of the infectivity of AcMNPV variants in *S. frugiperda* neonates.

| | | Fiducial Limits | | |
|---|---|---|---|---|
| Virus | $LC_{50}$ | Upper | Lower | Slope |
| L-1 | $4.6 \times 10^5$ | $6.8 \times 10^5$ | $3.0 \times 10^5$ | 0.81 |
| V-8 | $3.0 \times 10^5$ | $4.3 \times 10^5$ | $2.0 \times 10^5$ | 0.97 |
| vEcoRIHybI | $5.5 \times 10^5$ | $1.3 \times 10^6$ | $1.9 \times 10^5$ | 0.96 |
| vEcoRIHybIFS | $2.1 \times 10^5$ | $2.9 \times 10^5$ | $1.4 \times 10^5$ | 1.06 |

$LC_{50}$s (#PIBs/ml diet; polyhedria inclusion bodies/ml) for L-1, V-8, vEcoRIHybI, and vEcoRIHybIFs were statistically equivalent.

TABLE 1B

Bioassays of the Virulence of AcMNPV Variants in *S. frugiperda* neonates

| | | Fiducial Limits | | |
|---|---|---|---|---|
| Virus | $LT_{50}$ | Upper | Lower | Slope |
| L-1 | 129.4 | 134.1 | 125.7 | 12.35 |
| V-8 | 113.3 | 116.1 | 110.8 | 14.39 |
| vEcoRIHybI | 116.0 | 120.7 | 113.7 | 10.64 |
| vEcoRIHybIFS | 115.0 | 117.9 | 112.3 | 13.50 |

(B) The $LT_{50}$s (in hours) at $LC_{90}$ of V-8, vEcoRIHybI, and vEcoRIHybIFS were 10–12% faster than the $LT_{50}$ of L-1 at $LC_{90}$; this difference is statistically significant, as evidenced by the upper and lower fiducial limits.

The AcMNPV V-8 was genetically modified to inactivate the egt gene (egt encodes ecdysteroid glycosyl transferase)

following substantially the same procedure as described in U.S. Pat. No. 5,180,581. Then the $LT_{50}$ values were determined using *S. frugiperda* neonates for AcMNPV L-1, the egt-deficient derivative of L-1 (vEGTDEL), AcMNPV V-8 and the V-8 derivative in which the egt gene was inactivated (V8vEGTDEL). The results are shown in Tables 2 and 3. Clearly, AcMNPV V-8 killed faster than L-1, and V8vEGTDEL killed even faster than the AcMNPV V-8.

In diet overlay bioassays using second instar H virescens larvae, $LT_{50}$ values for V8vEGTDEL were lower than for the corresponding V-8 virus, and V-8 had lower $LT_{50}$ values than the L-1 strain. The vEGTDEL and V-8 had similar $LT_{50}$ values, and V8vEGTDEL had lower $LT_{50}$ than vEGTDEL (L-1). Using diet overlay tests with second instar *Helicoverpa zea* larvae, V8vEGTDEL exhibited significantly faster killing than AcMNPV E2. In insect larval tests, V8vEGTDEL appeared to kill infected insects faster than the AcMNPV L-1 egt-deletion strain (vEGTDEL). $LC_{50}$ values calculated on PIBs/16 $cm^2$ arena in diet overlay bioassays for

TABLE 2

| *S. frugiperda* neonate bioassays | | | | | |
|---|---|---|---|---|---|
| Virus | V-8 | V8vEGTDEL isolate 1 | L-1 | vEGTDEL | V8vEGTDEL isolate 2 |
| A. Dose $2 \times 10^7$ PIB/ml (100% mortality) | | | | | |
| Upper limit | 90 | 75.7 | 106 | 86.8 | 77 |
| LT50 | 84 | 70.6 | 103.6 | 81.5 | 72 |
| Lower limit | 84 | 66 | 101 | 76.5 | 68 |
| B. Dose: $5 \times 10^6$ PIB/ml (92% to 100% mortality) | | | | | |
| Upper limit | 91.8 | 83 | 109 | 101 | 85.5 |
| LT50 | 86.4 | 76.5 | 105 | 93 | 79 |
| Lower limit | 81 | 70.6 | 102 | 85.6 | 73 |

TABLE 3

| Bioassays of $LT_{50}$s V-8, L-1 and egt deletion in *S. frugiperda* neonates | | | | |
|---|---|---|---|---|
| Virus | Upper Limit | LT50 | Lower Limit | Skill |
| A. | | | | |
| V8vEGTDEL | 81.6 | 75.4 | 69.8 | 96 |
| V-8 | 99.6 | 95 | 91 | 90 |
| B. | | | | |
| L-1 | 106 | 102 | 98 | 90 |
| vEGTDEL | 89.7 | 84.2 | 78.9 | 96 |

AcMNPV wild-type strains (as E2 or L-1) were $1\times10^5$ to $1\times10^6$ for *S. frugiperda* and *H. zea*; $1\times10^3$ to $1\times10^4$ for *S. eridania*; and $1\times10^1$ to $1\times10^2$ for *T. ni, S. exigua* and *H. virescens*.

The V-8 isolate was further characterized by diet incorporation bioassays on neonate *S. frugiperda* and *T. ni*. The $LC_{50}$s were comparable, if not identical, in both insects, and the $ET_{50}$ of both isolates was the same in *T. ni* larvae. However, the $ET_{50}$ of the V-8 isolate was significantly faster than L-1 for *S. frugiperda* larvae.

Sequence analysis of a 1.8 kb portion of the EcoRI-I fragment that flanked the novel HindIII site of V-8 revealed a total of 73 nucleotide differences including four areas of insertions from lef-2 to the N-terminus of polh. The L-1 sequence of this same region was found to be identical to the C6 isolate of AcMNPV (Ayers et al. [1994] supra). The HindIII restriction polymorphism in V-8 resulted from a C to T mutation of the equivalent C6 nucleotide #4773. Both the MluI site at C6 nucleotide #3815 in ORF 603 and the EcoRV site at C6 nucleotide #4427 between polh and ORF 603 differed in V-8 (Table 7).

The V-8 virus had four insertions within or just upstream of the 603 ORF (Table 7). A 26 bp insert with ORF 603 created a stop codon in the reading frame and causes premature termination during ORF 603 translation. The L-1 ORF 603 sequence was used to search GenBank for other comparable baculovirus sequences, i.e., ORF 603 homologs. A corresponding ORF of 633 nucleotides was found in *Anagrapha falcifera* NPV (AfMNPV) between lef-2 and polh (Federici and Hice [1997] *Arch Virol.* 142:333–348). AfMNPV has the same four insertions that V-8 does (Table 7) except that, instead of having a 26 bp insert in ORF 603, there is only a 24 bp insert which keeps the comparable ORF 633 in frame. The AfMNPV 633 ORF has 98.3% identity to that of V-8 and 92.7% identity to the L-1 ORF 603 at the nucleotide level. AfMNPV has additional differences from L-1 beyond lef-2 and ORF 603. No ORF 603 homologs were found in the complete sequences of the *Bombyx mori* NPV (accession #L33180) or *Orgyia pseudotsugata* NPV (Ahrens and Rohrmann [1995] supra), genomes consistent with the observation of Gearing and Possee (1990) *J. Gen. Virol.* 71:251–262 that ORF 603 is an accessory gene for baculoviruses rather than an essential gene. Geary and Possee, however, reported no phenotypic effect associated with loss of function for ORF 603 in AcMNPV.

No sequence differences between V-8 and L-1 AcMNPV were discovered in the sequenced portion of ORF 5. Only two sequence differences were discovered in V-8 polh up to the BamHI site (nucleotide #4690) when compared to the L-1 sequence, both of which were third base pair silent mutations. The promoter region of polh was unchanged. The complete sequence of the protein tyrosine/serine phosphatase gene (ptp) (ORF 1) was also compared to L-1, but no differences were detected.

We were interested in determining which, if any, of the mutations within this region was responsible for the decreased $ET_{50}$ of the V-8 virus. Because the most striking difference between V-8 and L-1 was the predicted truncation of the V-8 603 ORF, we therefore introduced a frameshift mutation into the 603 ORF of the L-1 by allelic recombination of the L-1 EcoRI-I fragment, frameshifted at the NgoAIV site, with the L-1-based virus vSynVI$^-$gal (Wang et al. [1991] *Gene* 100:131–137); (FIG. 4A). Since vSynVI$^-$ had been passaged several times in cell culture, a revertant was also constructed by recombining a plasmid containing the EcoRI-I fragment of L-1 with vSynVI$^-$gal to ensure that the viruses were directly comparable. Wild type viruses obtained from this cross are referred to as L-1 revertants. Two independent isolates of both the L-1 revertant and the L-1 603 frameshift recombinants were isolated and tested in bioassays. The infectivity and virulence of these viruses were compared to duplicate stocks of the V-8 isolate in *S. frugiperda* (Table 8). The $LC_{50}$s of all three viruses were found to be similar if not identical. However, the V-8 and 603 frameshift viruses had a significantly lower $ET_{50}$ than the L-1 revertant virus, indicating that the truncated ORF 603 is responsible for the decreased $ET_{50}$ of V-8.

Although we considered the possibility that the V-8 variant expressing the insect-selective toxin tox34, and lacking egt might be a more effective pesticide than the L-1 variant expressing tox34, there was no significant difference in the $ET_{50}$ of the toxin-expressing viruses, even when two different promoters were compared. Thus, toxin gene expression masks the effects of ORF 603 disruption in *S.*

*frugiperda*. The speed of action of viruses expressing tox34 may be approaching the limit of what is biologically achievable with regard to $ET_{50}$ reduction (Black et al. [1997] Commercialization of Baculoviral Insecticides; In "The Baculoviruses" [L. K. Miller, Ed.], pp. 341–381. Plenum Press, New York).

The most striking difference in V-8 as compared with AcMNPV L-1 was the truncation of the product of the ORF 603. The region encompassing lef-2 and ORF 603 of V-8 contained an unexpectedly high density of mutations, considering the restriction endonuclease patterns which reflect the conservation of sequence throughout the rest of the genome. This suggests the possibility that V-8 arose by recombination between AcMNPV and another AcMNPV-like baculovirus such as Anagrapha falcifera multinucleocapsid nuclear polyhedrosis virus (AfMNPV) (Federici and Hice [1997] *Arch. Virol.* 142:333–348) or Rachiplusia ou MNPV (Jewell and Miller [1980] *J. Gen. Virol.* 48:161–176) rather than from random point mutations and insertions in L-1. Considering the distributions of mutations in this region, the differences in lef-1 and ORF 603 appear to make the limits of the recombination event, as no sequence differences were found downstream of the BamHI site of polh and upstream of lef-2 to the MluI site within ORF 5 (FIGS. 4A–4D). Complete sequence analysis of ptp (ORF 1) also revealed no differences between L-1 and V-8.

By constructing an L-1 virus derivative with a frameshift in ORF 603, we correlated the increased virulence of the V-8 variant in *S. frugiperda* with the functional inactivation of this ORF. The infectivities ($LC_{50}$s) of L-1 and V-8 were very similar, but the $ET_{50}$ of the V-8 variant was approximately 10% shorter than L-1, reflecting increased virulence (Table 7). The $LC_{50}$ of the L-1 ORF 603 frameshift virus was also similar to V-8 and L-1 but the $ET_{50}$ was similar to V-8 indicating that the loss of the ORF 603 product results in increased virulence of the virus in this species. It has been previously shown that the ORF 603 is nonessential for production of budded virus in cell culture, production of polyhedra, and the infectivity of AcMNPV in *T. ni* larvae (Gearing and Possee [1990] supra). The actual role of the ORF 603 product in virus infection remains unknown. Without wishing to be bound by theory, it is believed to have a host-specific function.

Figure 5A:
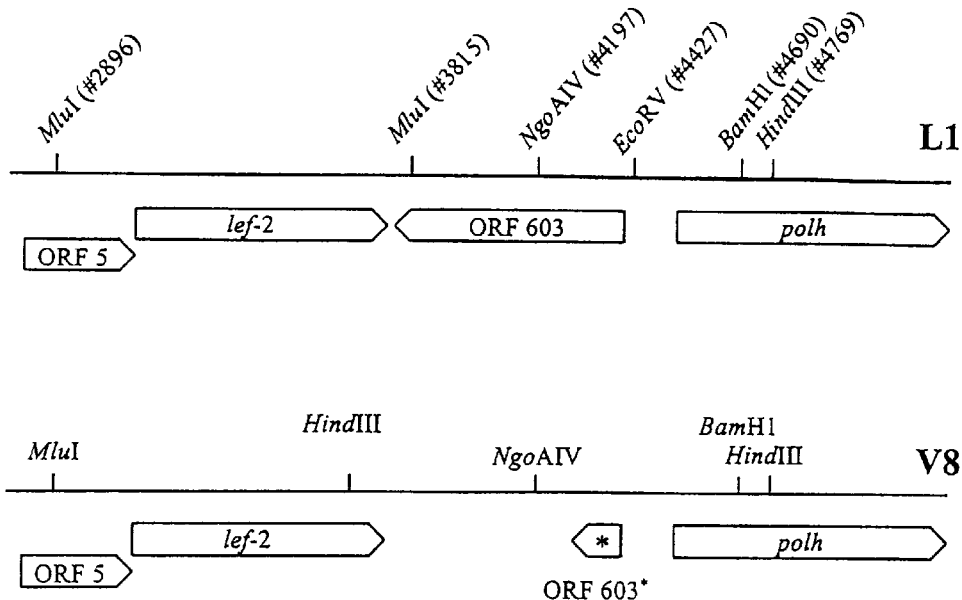
FIG. 5A is a diagram showing the partial restriction map of ORF 5, lef-2, ORF 603, and polh in the L-1 and V-8 isolates of AcMNPV. The extra HindIII site with lef-2 is characteristic of V-8 which is also missing both the MluI site with ORF 603 and the EcoRV site between ORF 603 and polh. The V-8 ORF 603 has a premature stop codon generated by an insertion and is predicted to produce an incomplete, non-functional polypeptide product (ORF 603*).
Figure 5B:
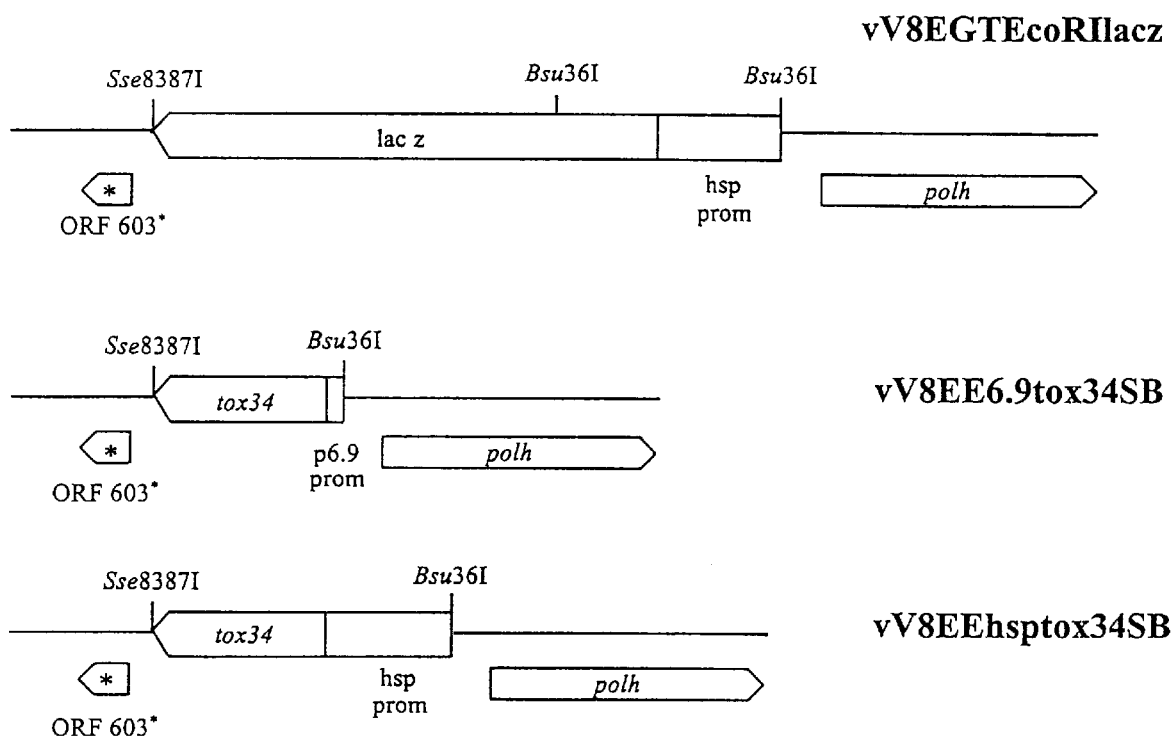
FIG. 5B is a diagram showing the polh region of baculovirus recombinants with either the E. coli lacZ or tox34 inserted in the V-8 genome upstream and in the opposite orientation to polh. Insertions were made at nucleotide #4427 where the EcoRV site is in the C6 variant (Ayers et al. [1994] Virology 202:586–605). Sequence numbering in parentheses corresponds to that in O'Reilly et al. (1992) Baculovirus Expression Vectors: A Laboratory Manual. W. H. Freeman & Co., N.Y.

In an effort to further improve the AcMNPV virus by combining the technologies of toxin insertion, egt deletion, and 603 ORF modification (inactivation), two viruses were constructed in the V-8 background that contained a deletion in egt and had tox34 inserted under the control of either the late viral p6.9 or the Drosophila HSP70 promoter (FIG. 5B). The promoters have been shown to be excellent promoters for driving toxin gene expression in AcMNP (Lu et al. [1996] supra). The viruses, V8EEp6.9tox34 and V8EEHSPtox34, were then compared with L-1 viruses with tox34 inserted in the same genomic position and under the control of the same promoters, v6.9tox34 and vHSP70tox34 (Table 10). The V-8 and V8EGTdel viruses served as controls. The $LC_{50}$s were identical for all these viruses. All viruses expressing tox34 had strikingly reduced $ET_{50}$s compared to V-8 or V8EGTdel. The $ET_{50}$s of vV8EE6.9tox34SB (lacking functional ORF 603 and EGT (proteins) was not significantly different from the L-1 derivative v6.9tox34 (containing functional ORF 603 and EGT). The $ET_{50}$ of vV8EEHSPtox34SB was slightly lower than that of vHSP70tox34 at an $LC_{95}$ dose. A higher dose of virus was needed to lower the $ET_{50}$ of all viruses (Table 7).

Thus, preferred viruses for insect control carry both an inactivated ORF 603 or an inactivated ORF 603 homolog and a genetic modification inactivating the gene encoding ecdysteroid glycosyl transferase. Functional equivalents of the AcMNPV ORF 603 from other baculoviruses can be readily identified, isolated and inactivated using the teachings of the present disclosure and technology well known to the art.

AcMNPV, which has been used as a model system for much baculovirus research, interferes with the process of insect development. Insect larvae infected with AcMNPV are no longer able to molt or pupate because AcMNPV directs the synthesis of an enzyme, known as ecdysteroid UDP-glycosyltransferase (EGT), which specifically inactivates the insect ecdysteroids (molting hormones) by conjugating them to galactose in vivo (O'Reilly et al. [1991] *Insect Biochem. Molec. Biol.* 22:313–320) or glucose in vitro (O'Reilly et al. [1990] *Science* 245:1110–1112). Other baculoviruses carry egt genes as well.

Figure 1B:
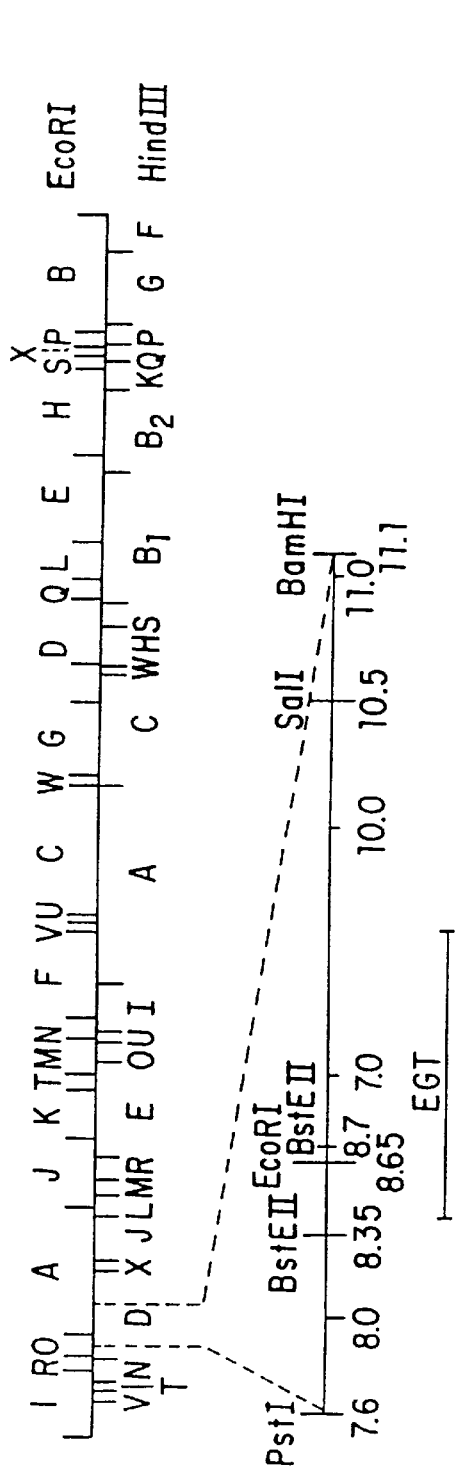
Figure 1C:
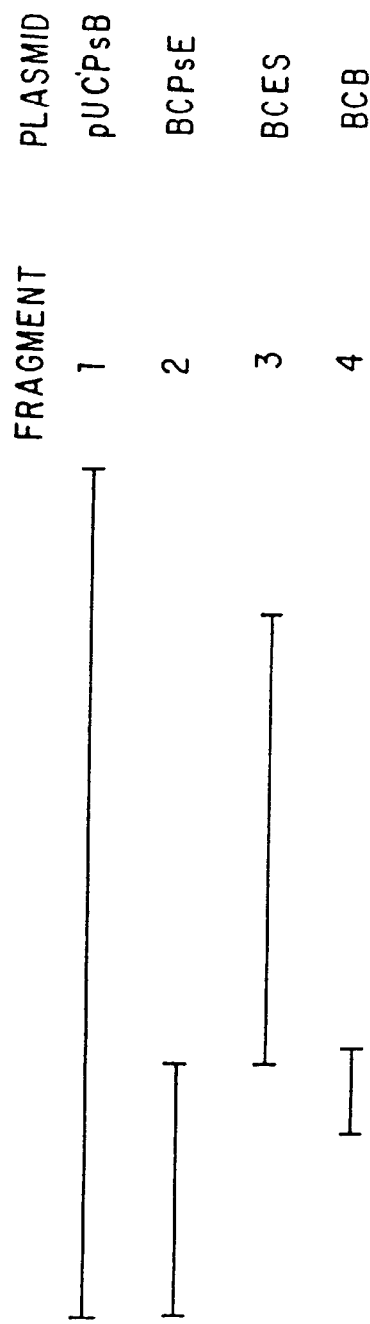

The AcMNPV gene encoding EGT extends from 8.4 to 9.6 map units on the AcMNPV genome (FIGS. 1 and 2). FIG. 2 shows the restriction map of the egt region of the genome. The nucleotide sequence of the AcMNPV (strain L-1) egt gene is shown in SEQ ID NO:5. The coding sequence of egt extends from nucleotide 149 to nucleotide 1670. See also U.S. Pat. No. 5,180,581.

In one embodiment of the present invention, the egt gene of the AcMNPV V-8 strain is inactivated by replacing a portion of the egt gene with a bacterial sequence encoding β-galactosidase. This recombinant baculovirus is designated V8vEGTDEL herein. In a second preferred embodiment, part of the egt gene of the V-8 strain AcMNPV is deleted without replacement, for example, by deleting an EcoRI/XbaI segment from within the egt coding sequence (See FIGS. 6A–6B; U.S. Pat. No. 5,180,581; Example 7 hereinbelow). An alternate mechanism for the inactivation of the insect virus egt gene is the insertion of a gene encoding an insect hormone affecting ecdysis, an enzyme which inactivates an insect hormone affecting ecdysis, which gene is expressible in an insect cell infected with said insect virus or an insect-specific toxin gene.

Using the AcMNPV egt gene as a probe, an egt gene has been identified in the baculovirus *Orgyia pseudotsugata* nuclear polyhedrosis virus (OpMNPV). It will be recognized by those skilled in the art with the benefit of this disclosure that the egt gene of any baculovirus can be characterized and isolated in a similar manner as AcMNPV (see, e.g., U.S. Pat. No. 5,180,581, incorporated by reference herein in its entirety). egt genes with at least 70% nucleotide sequence homology to the egt coding sequence in FIGS. 6A–6B from nucleotides 149 to 1666 (and in SEQ ID NO:5, from nucleotide 149 to 1666) are considered equivalent to said sequence, provided those homologous genes encode an enzyme which is an ecdysteroid UDP-glycosyl transferase, and their identification, isolation and manipulation will be readily achieved by the skilled worker using the sequences and assay information provided, taken together with what is well known in the art. Functional equivalents of the egt gene are those which also catalyze the inactivation of ecdysteroids such as ecdysone by transferring a glucose or galactose moiety from UDP-glucose to the ecdysteroid(s). Those functional equivalents of egt may be identified using the assay methods described herein. Baculoviruses lacking a functional egt gene are considerably more effective as insect control agents than wild-type baculoviruses. It will be apparent to those skilled in the art with the benefit of this disclosure that the egt gene can be rendered nonfunctional in any baculovirus by any means known to the art.

Although the length of time progeny virus can accumulate in larvae infected with baculoviruses lacking a functional egt gene is somewhat truncated and the infected insect displays reduced growth, there is substantial production of progeny virus. The amount of virus obtained per larva following vEGTZ infection of late instar larvae is about 15 to 50% that obtained with wt virus. This is sufficient to allow cost-effective preparation of large quantities of virus particles.

The gene encoding PTTH (a peptide hormone) can be inserted into the viral genome with the egt gene inactivated and PTTH can be expressed at levels sufficiently high to affect ecdysis. Insect larvae infected with such a virus experience extreme disruption in the hormonal control of development. These insects become sick rapidly resulting in severely compromised growth and development, reduced feeding, and earlier death. PTTH sequences are described in Kawakami et al. (1990) *Science* 247:1333.

It is important to note that, while all of the above genes could be added to wild-type virus genome using disclosure provided herein and/or in U.S. Pat. No. 5,180,581 or 5,266,317 and techniques well known to the art, they would not be expected to significantly affect insect behavior in the wild-type virus because expression of the egt gene by wild-type virus inactivates the ecdysteroid molting hormones and ecdysis is prevented, regardless of the production of other hormones. Thus, successful strategies involving the generation of viruses designed to interfere with insect ecdysis depend upon prior inactivation of the egt gene.

It will be understood by those skilled in the art that mutant ORF 603-deficient baculoviruses lacking an intact egt gene or incapable of expressing a functional egt product and those which are further genetically modified so as to express another hormone-modifying enzyme or a peptide developmental hormone are included as insect control agents of the present invention. Similarly, a baculovirus lacking functional 603 ORF can be further improved by genetically modifying it to contain and express an insect-specific toxin, coding sequences and promoters being readily available to the art.

An isolated and purified insect virus is one which has been cloned through plaque purification in tissue culture, for example, or otherwise prepared from a single viral genotype. A recombinant insect virus, as used herein, is one which has at least one portion of its genotype derived from a heterologous insect virus, i.e., an insect virus of different taxonomic viral species. A recombinant insect virus may be generated by co-infection of one insect cell or insect with one than one viral species, or it may be the result of introducing insect virus genomic DNA and a heterologous insect DNA virus segment into the same insect or insect cell, with the result that a portion of the heterologous DNA becomes incorporated in the insect virus genome by recombination process. It is understood in the art that such a recombinant virus can be recognized via restriction endonuclease analysis, DNA sequencing at least a portion of the putative recombinant genome or via a change in phenotype. As specifically exemplified herein, recombinant insect viruses are recognized by their increased virulence phenotype (lower $LT_{50}$) in at least one target insect as compared with the parental insect virus. A recombinant insect virus phenotype with the faster killing phenotype can be further genetically modified and further improved as an insect control agent by inactivating an ecdysteroid modifying enzyme, for example.

As used herein, an insecticidal composition has at least one active ingredient which has an adverse affect on insect pests, preferably which kills said pests. The present invention is the use of a recombinant baculovirus which has been isolated or which has been genetically engineered to kill at least one insect pest faster than the corresponding wild-type comparison baculovirus due to inactivation of an ORF 603 or ORF 603 homolog. When an Egt-deficient derivative of that recombinant baculovirus is used, feeding by insects is reduced in response to the insect egt-deficient recombinant virus, normal insect ecdysis is disrupted and death of the insect is further accelerated relative to the isogenic wild-type strain (i.e., with functional egt). A recombinant virus of this invention can also be an insect virus genetically engineered to inactivate a gene encoding an ecdysteroid modifying enzyme or one which is further engineered to express a heterologous gene encoding a protein which affects insect development, so as to minimize the time of insect feeding or to cause more rapid killing after virus infection.

It will be understood by those skilled in the art that the insect pests can be exposed to the viruses of the present invention by conventional methods including ingestion, inhalation or direct contact of the insect control agent.

A primary use of the recombinant and/or genetically engineered baculoviruses of the present invention will be as active ingredients of insecticidal compositions for applying to plants to effect the biological control of insect pests of plants. Many variations of preparing agriculturally suitable compositions for insect control are known in the art. The insecticidal compositions of this invention are typically administered at dosages in the range of $2.4 \times 10^8$ to $2.4 \times 10^{12}$ PIBs/hectare of recombinant insect virus.

Insecticidal compositions suitable for applications to plants to control insect pests comprise an agriculturally suitable carrier and a genetically engineered baculovirus. Conventional formulation technology known to persons skilled in the art is used to prepare the compositions of this invention. The compositions can be in the form of wettable powders, dispersible granular formulations, granules, suspensions, emulsions, solutions for aerosols, baits and other conventional insecticide preparations. Wetting agents, coating agents, agents to promote physical flexibility, UV protectants, dispersants and sticking agents are desirable additives in at least some formulations. The compositions will frequently include an inactive carrier, which can be a liquid such as water, alcohol, hydrocarbons or other organic solvents, or a mineral, animal or vegetable oil, or a powder such as talc, clay, silicate or kieselguhr. A nutrient such as sugar may be added to increase feeding behavior and/or to attract insects. Flow agents, for example, clay-based flow agents, may be added to minimize caking of the wettable powders or other dry preparations during storage. Application of an insecticidal composition of this invention can protect plants from insect pests by reducing feeding by and killing of susceptible insects. Wettable powder formulations are described hereinbelow.

The skilled artisan knows how to choose a baculovirus which is suitable for the control of a particular insect pest. The concentration of the baculovirus that will be required to produce insecticidally effective agricultural compositions for plant protection will depend on the type of crop, target insect, virus genotype used and the formulation of the composition. Insecticidal compositions may be formulated, for example, as wettable powders, with about 10% (w/w) polyhedrin inclusion bodies. The insecticidally effective concentration of the insect control agent within the composition can readily be determined experimentally by a person of ordinary skill in the art.

Agricultural compositions must be suitable for agricultural use and dispersal in fields. Generally, components of the composition must be non-phytotoxic and not detrimental to the integrity of the occluded virus. Foliar applications must not damage or injure plant leaves. In addition to appropriate solid or, more preferably, liquid carriers, agricultural compositions may include sticking and adhesive agents, emulsifying and wetting agents, but no components which deter insect feeding or any viral functions. It is desirable to add components which protect the insect control agent from UV inactivation. Agricultural compositions for insect pest control may also include agents which stimulate insect feeding.

Reviews describing methods of application of biological insect control agents and agricultural application are available. See, for example, Couch and Ignoffo (1981) in *Microbial Control of Pests and Plant Disease 1970–1980*, Burges (ed.), chapter 34, pp. 621–634; Corke and Rishbeth, ibid, chapter 39, pp. 717–732; Brockwell (1980) in *Methods for Evaluating Nitrogen Fixation*, Bergersen (ed.) pp. 417–488; Burton (1982) in *Biological Nitrogen Fixation Technology for Tropical Agriculture*, Graham and Harris (eds.) pp. 105–114; and Roughley (1982) ibid, pp. 115–127; *The Biology of Baculoviruses*, Vol. II, supra.

Field trials in which AcMNPV E-2, V8vEGTDEL and a commercial *Bacillus thuringiensis* subsp. kurstaki insecticide (DIPEL 2X, Abbott Laboratories, Chicago, Ill.) were carried out during the fall growing season in Arizona. Although the pest infestation was relatively light, results from this study indicated that V8vEGTDEL was efficacious against *T. ni* in young lettuce (Table 4). Following the fourth application of treatments (on ca. 5-day intervals), V8vEGTDEL at $1\times10^{11}$ and $1\times10^{12}$ PIBs/A provided better control of *T. ni* than similar doses of AcMNPV-E2 "wild-type". Additionally, V8vEGTDEL at $1\times10^{11}$ and $1\times10^{12}$ PIBs/A provided control of the *T. ni* infestation at levels equal to that provided by DIPEL 2X at 1 lb/A. Based on data collected after only three applications, however, DIPEL 2X provided better pest control than either baculovirus.

After completion of data collection, the test site (as well as 10-ft wide perimeter) was sprayed with an aqueous dilution of 1% (v/v) bleach. The treated crop, as well as a 10-ft wide perimeter, was then destroyed by using tractor-mounted tillage equipment. About 3 weeks later, soil samples were collected from several sites located within 100 ft of the test site. No V8vEGTDEL virus were detected in soil surrounding the test site, and no additional action was taken.

In a second fall field trial, the efficacy of V8vEGTDEL, AcMNPV E2 and a commercial *B. thuringiensis* subsp. kurstaki insecticide (DIPEL 2X, Abbott Laboratories, Chicago, Ill.) against the cabbage looper in New Jersey. Viral insecticidal compositions were formulated as wettable powders.

TABLE 4

Efficacy of selected baculovirus treatments against *Trichoplusia ni* in lettuce

| Treatment[1] | Dose/A[2] | Mean # larvae/10 plants at 3DA3T | Mean # larvae/10 plants at 5DA4T |
|---|---|---|---|
| V8vEGTDEL | $1 \times 10^{10}$ PIBs | 15 ab[3] | 20 a |
| | $1 \times 10^{11}$ PIBs | 20 a | 2 c |
| | $1 \times 10^{12}$ PIBs | 12 b | 7 bc |
| AcMNPV E2 | $1 \times 10^{10}$ PIBs | 10 b | 18 a |
| | $1 \times 10^{11}$ PIBs | 18 a | 20 a |
| | $1 \times 10^{12}$ PIBs | 12 b | 10 b |

TABLE 4-continued

Efficacy of selected baculovirus treatments against *Trichoplusia ni* in lettuce

| Treatment[1] | Dose/A[2] | Mean # larvae/10 plants at 3DA3T | Mean # larvae/10 plants at 5DA4T |
|---|---|---|---|
| DIPEL 2X | 1 lb form | 0 c | 7 bc |
| Untreated | — | 20 a | 18 a |

[1] Baculovirus compositions were formulated as water-soluble wettable powders ($1 \times 10^{11}$ PIBs/10 gm).
[2] Baculovirus compositions were applied at $1 \times 10^{E9}$, $1 \times 10^{11}$, and $1 \times 10^{13}$ PIBs/A on day 15, however, due to poor mixing and spray characteristics of the $1 \times 10^{13}$ dose, both baculovirus were applied at $1 \times 10^{10}$, $1 \times 10^{11}$ and $1 \times 10^{12}$ PIBs/A in all subsequent applications at days 5, 10 and 15. DIPEL 2X was also applied on days 1, 5, 10 and 15.
[3] Means within columns followed by the same letter are not significantly different (DMRT, P = 0.05).

Due to the light pest infestation in this study, differences among treatments in control of *T. ni* larvae were very slight (and generally not statistically significant). However all treatments had significantly fewer live larvae and less plant defoliation than untreated cabbage (Table 5). At 7 days after last application of treatments, untreated plots averaged 18% defoliation whereas cabbage treated with V8vEGTDEL or AcNPV-E2 "wild type" (rates of $1\times10^9$, $1\times10^{11}$, and $1\times10^{12}$ PIBs/A) averaged 8–10% defoliation and DIPEL-treated (1 lb/A) cabbage averaged 4% defoliation. At 12 days after last application, untreated plots had a mean of 6.5 live larvae/10 plants whereas baculovirus-($1\times10^{11}$ and $1\times10^{12}$ PIBs/A) and DIPEL-treated plots averaged <2 larvae/10 plants.

After data collection was complete, the test site (as well as 10-ft wide perimeter) was sprayed with an aqueous dilution of 1% (v/v) bleach. The treated crop, as well as a 10-ft wide perimeter, was then destroyed by using tractor-mounted cultivation equipment. About five months after the bleach treatment, soil samples were again collected from several sites located within 100 ft of the test site. Also on this date, the test site was treated with AcMNPV-E2 "wild-type" at a rate of $1\times10^{12}$ PIBs/A. No V8vEGTDEL was detected in these later soil samples.

TABLE 5

Efficacy of selected baculovirus treatments against *Trichoplusia ni* in cabbage

| Treatment[1] | Dose/A[2] | Mean # larvae/10 plants at 7DA3T | Mean # larvae/10 plants at 12DA3T |
|---|---|---|---|
| V8vEGTDEL | $1 \times 10^9$ PIBs | 10 b[3] | 2.0 b |
| | $1 \times 10^{11}$ PIBs | 11 b | 1.2 bc |
| | $1 \times 10^{12}$ PIBs | 7 bc | 1.7 bc |
| AcMNPV E2 | $1 \times 10^9$ PIBs | 8 bc | 2.0 b |
| | $1 \times 10^{11}$ PIBs | 8 bc | 0.8 bc |
| | $1 \times 10^{12}$ PIBs | 11 b | 0.8 bc |
| DIPEL 2X | 1 lb form | 4 c | 0.2 c |
| Untreated | — | 8 a | 6.5 a |

[1] Both types of baculoviruses were formulated as water-soluble wettable powders (1E11 PIBs/10 gm of WP).
[2] "EGT-deleted" and "Wild-type" (at $1 \times 10^9$ and $1 \times 10^{11}$ PIBs/A) and DEPEL 2X were applied three times. Due to severe clogging of nozzles, the planned baculovirus does of $1 \times 10^{13}$ PIBs/A, so no baculovirus "high dose" was applied at the first application and V8vEGTDEL and AcMNPV E2 at $1 \times 10^{12}$ PIB/A were applied and were subsequently applied only twice (5 and 10 days later).
[3] Means within columns followed by the same letter are not significantly different (DMRT, P = 0.05).

A third field trial for efficacy of V8vEGTDEL, AcMNPV E2 and a commercially available *B. thuringiensis* subsp. awaizai insecticide (XENTARI, Abbott Laboratories, Chicago, Ill.) for control of *T. ni* in lettuce was carried out in spring in Florida.

The data are summarized in Table 5. V8vEGTDEL provided significantly faster control of *T. ni* than AcMNPV V-8. Five days after treatment with V8vEGTDEL ($1 \times 10^{12}$ PIBs/A) caused 100% larval mortality whereas V-8 at the same dose caused only 29% larval mortality (up to 97% mortality by day 7). Also, V8vEGTDEL ($1 \times 10^{11}$ PIBs/A) exhibited larval control at a rate equal to that of V-8 at $1 \times 10^{12}$ PIBs/A.

The commercial XENTARI (1 lb form./A), provided 76% larval control by day 4 vs. only 40% larval control from V8vEGTDEL ($1 \times 10^{12}$ PIBs/A). However, by day 5, V8vEGTDEL ($1 \times 10^{12}$ PIBs/A) and XENTARI (1 lb/A) exhibited 100% and 89% larval mortality, respectively.

TABLE 6

Efficacy of field applications of V8vEGTDEL and AcMNPV V-8 against *Trichoplusia ni* in lettuce

| Treatment | Dose per acre | Mean # larval mortality[2] | | | |
|---|---|---|---|---|---|
| | | Day 4 | Day 5 | Day 6 | Day 7 |
| V8vEGTDEL | $1 \times 10^{11}$ PIBs | 0 | 35 | 88 | 100 |
| V8vEGTDEL | $1 \times 10^{12}$ PIBs | 40 | 100 | — | — |
| AcMNPV V-8 | $1 \times 10^{12}$ PIBs | 4 | 29 | 68 | 97 |
| Xentari | 1 lb | 76 | 89 | 92 | 95 |

[1]Baculovirus compositions were formulated as wettable powder.
[2]Treatments were applied to six true-leaf lettuce (4 plots/treatment, RCT design). About 3 hrs. after application, leaves were harvested from field-plots, individually placed into petri dishes containing water-moistened filter paper, and then infested with three-day-old *T. ni* larvae (ca. 10 larvae/leaf). Two days later, larvae were placed in CD-International trays containing untreated Stoneville artificial diet (1 larva/diet-well), and percent mortality was rated on each of several days post-treatment.

The examples provided herein use many techniques well known and accessible to those skilled in the art of molecular biology. Enzymes are obtained from commercial sources and are used according to the vendors' recommendations or other variations known to the art. Reagents, buffers and culture conditions are also known to the art. Baculovirus procedures are described in O'Reilly et al. (1992) *Baculovirus Expression Vectors: A Laboratory Manual.* W. H. Freeman and Company, New York, N.Y. References providing standard molecular biological procedures include Sambrook et al. (1989) *Molecular Cloning*, second edition, Cold Spring Harbor Laboratory, Plainview, N.Y.; R. Wu (ed.) (1993) *Methods in Enzymology* 218; Wu et al. (eds.)

TABLE 7

Time mortality response of neonate *Spodoptera frugiperda* larvae infected per os in the droplet feeding assay with the V-8 isolate, a 603 frameshift mutant of L-1 and an L-1 revertant of AcMNPV

| | Dose Response[a] | | | | | Time Response[b] | |
|---|---|---|---|---|---|---|---|
| Virus | $LC_{50}$ (PIB/ml) | 95% Fiducial Limit | | Slope | Hetero-geneity | $ET_{50}$ (hr ± SE) | Slope (± SE) |
| | | Lower | Upper | | | | |
| V-8 | $1.6 \times 10^4$ | $1.9 \times 10^3$ | $6.2 \times 10^4$ | $1.3 \pm 0.2$ | 1.3 | $88.5 \pm 2.2$ | $13.1 \pm 2.1$ |
| V-8 | $1.3 \times 10^4$ | $3.5 \times 10^3$ | $3.0 \times 10^4$ | $0.9 \pm 0.2$ | 0.3 | $88.0 \pm 1.8$ | $16.0 \pm 2.06$ |
| 603 frame-shift #1 | $2.2 \times 10^4$ | $1.1 \times 10^4$ | $4.3 \times 10^4$ | $1.4 \pm 0.2$ | 1.1 | $89.5 \pm 1.7$ | $17.3 \pm 3.0$ |
| 603 frame-shift #2 | $4.1 \times 10^4$ | $1.4 \times 10^4$ | $9.2 \times 10^4$ | $0.9 \pm 0.2$ | 0.5 | $83.4 \pm 1.9$ | $14.8 \pm 2.4$ |
| L-1 revert-ant #1 | $3.1 \times 10^4$ | $1.3 \times 10^4$ | $6.2 \times 10^4$ | $1.2 \pm 0.2$ | 0.0 | $100.8 \pm 2.7$ | $12.1 \pm 2.7$ |
| L-1 revert-ant #2 | $1.1 \times 10^4$ | $4.9 \times 10^3$ | $2.0 \times 10^4$ | $1.5 \pm 0.3$ | 0.0 | $97.2 \pm 2.8$ | $11.8 \pm 2.0$ |

[a]Determined by Probit analysis
[b]Determined by ViStat 2.1 analysis.

TABLE 8

Response of neonate *S. frugiperda* larvae to oral infection with the V-8 isolate of AcMNPV and recombinant viruses expressing the tox34 under control of alternate promoters.

| | Dose Response[a] | | | | | Time Response[b] | | | |
|---|---|---|---|---|---|---|---|---|---|
| | $LC_{50}$ | 95% Fiducial Limit | | | Hetero- | $LC_{70}$ | | $LC_{95}$ | |
| Virus | (PIB/ml) | Lower | Upper | Slope | geneity | ET50 ± SE | Slope ± SE | ET50 ± SE | Slope ± SE |
| V-8 | $1.6 \times 10^5$ | $1.1 \times 10^5$ | $2.3 \times 10^5$ | $1.2 \pm 0.1$ | 0.1 | $117.4 \pm 4.6$ | $10.7 \pm 2.1$ | $108.0 \pm 1.8$ | $14.4 \pm 1.7$ |
| vV8EGTdel | $2.5 \times 10^5$ | $1.9 \times 10^5$ | $3.3 \times 10^5$ | $1.5 \pm 0.1$ | 0.7 | $107.0 \pm 4.3$ | $7.0 \pm 1.0$ | $88.2 \pm 2.8$ | $7.4 \pm 0.9$ |
| vp6.9tox34 | $1.1 \times 10^5$ | $5.6 \times 10^4$ | $1.9 \times 10^5$ | $1.4 \pm 0.2$ | 1.2 | $69.5 \pm 2.3$ | $8.7 \pm 1.3$ | $55.6 \pm 1.0$ | $13.4 \pm 1.6$ |
| vV8EEp6.9tox34 | $2.7 \times 10^5$ | $1.6 \times 10^5$ | $4.5 \times 10^5$ | $1.5 \pm 0.2$ | 1.2 | $72.3 \pm 2.1$ | $9.2 \pm 1.3$ | $58.2 \pm 1.5$ | $9.1 \pm 1.1$ |
| vHSP70tox34 | $3.2 \times 10^5$ | $1.8 \times 10^5$ | $5.8 \times 10^5$ | $1.4 \pm 0.1$ | 1.4 | $66.0 \pm 3.0$ | $6.6 \pm 1.0$ | $59.3 \pm 1.3$ | $11.5 \pm 1.3$ |
| vV8EEHSPtox34 | $2.1 \times 10^5$ | $1.5 \times 10^5$ | $2.8 \times 10^5$ | $1.4 \pm 0.1$ | 0.2 | $62.9 \pm 2.4$ | $8.0 \pm 1.2$ | $51.2 \pm 0.8$ | $14.4 \pm 1.8$ |

[a]Determined by Probit analysis
[b]Determined by ViStat 2.1 analysis

*Methods in Enzymology* 100, 101; Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. Abbreviations and nomenclature, where employed, are deemed standard in the field and are commonly used in professional journal such as those cited herein. All references cited in the present application are expressly incorporated by reference herein to the extent that they are not inconsistent with the present disclosure.

This invention is illustrated by the following examples, which are not to be construed in any way as imposing limitations on the scope thereof. It is understood that resort may be had to various other embodiments, modifications, and equivalents thereof which, after reading the description herein, may suggest themselves to those skilled in the art without departing from the spirit of the present invention and/or the scope of the appended claims.

THE EXAMPLES

Example 1

Isolation of AcMNPV V-8

A minimally passaged AcMNPV stock from the original AcMNPV (Vail et al. [1971] Proc. IV Int. Colloq. Insect Pathology, College Park, Md. pp. 297–304) was amplified in *Heliothis virescens* larvae from the *H. virescens* colony at American Cyanamid, Princeton, N.J. The *H. virescens* are reared on a soybean-wheat germ agar-based diet at 28 C under constant fluorescent light. Virus was then further amplified in *H. virescens* larvae. Ten viral clones were plaque-purified from diluted hemolymph from the latter infected *H. virescens* larvae. Methods for plaque assay, plaque purification, virus amplification and viral DNA preparation are described in O'Reilly et al. (1992) *Baculovirus Expression Vectors; A Laboratory Manual*, W. H. Freeman & Co., New York, N.Y. Unless otherwise indicated, viruses were propagated at 27° C. in the IPLB-SF-21 cell line (SF-21) (Vaughn et al., [1977] *In Vitro* 13:213–217) using TC100 medium (Gibco BRL, Gaithersburg, Md.) supplemented with 0.26% tryptose broth and 10% fetal bovine serum (Intergen, Purchase, N.Y.). SF-21 cells are commercially available (e.g., Invitrogen Corporation, San Diego, Calif.). DNA was prepared from each isolate and characterized by restriction endonuclease analysis in parallel with DNA prepared from the L-1 strain of AcMNPV, which is described in Lee and Miller (1978) *J. Virol.* 27:754.

The L-1 strain of AcMNPV (Lee and Miller [1978] supra) served as the wild-type virus and parental virus for the recombinant viruses v6.9tox34 and vHSP70tox34 which contain tox34 under the control of the late 6.9K viral promoter (Lu et al. [1996] *J. Virol.* 70:5123–5130) or the HSP70 promoter of *Drosophila melanogaster* Meigen, respectively (McNitt et al. [1995] *Biol. Control.* 5:267–278). Isolation of the V-8 variant was performed as follows: SF21 cells were inoculated with diluted hemolymph from *Heliothis virescens* (Fabricius) larvae that had been orally infected with a minimal passage occluded virus stock of the original Vail Isolate (Vail et al. [1973] *J. Invert. Pathol.* 17:383–388; Vail et al. [1971] supra). This virus stock was provided by American Cyanamid (Princeton, N.J.) and had been passed only once through *H. virescens* larvae (Stoneville, Miss.). The DNA from the viruses amplified from ten plaques derived from this single plaque purification were characterized by the restriction endonucleases BamHI, BglII, EcoRI, HindIII, PstI, and XhoI and compared to L-1 DNA similarly digested. The majority of these isolates had an additional HindIII site in the EcoRI-I fragment when compared to L-1. The isolate designated V-8 was chosen as representative of the predominate genotype of the ten isolates. It was deposited in the American Type Culture Collection, Manassas, Va., as ATCC VR2465.

Example 2

Analysis of the AcMNPV lef-2 and 603 ORF Region

Molecular biology techniques were used as previously described (Maniatis et al. [1989] supra). Plasmid pRI-I contains the 7.33 kb AcMNPV L-1 EcoRI-I fragment cloned in the EcoRI site of pBR322. Plasmid pEcoRI-IV8 contains the V-8 EcoRI-I fragment in the EcoRI site of Bluescript KS+ (Stratagene, La Jolla, Calif.). Plasmid pEcoRIHybI was constructed by replacing the 1.72 kb MluI to EspI fragment (1.93–3.27 m.u.) in the L-1 EcoRI-I fragment with the corresponding fragment from V-8. The hybrid EcoRI-I fragment was then recloned into a pUC19 vector, producing pUC19HybI, a plasmid with a unique NaeI site in the 603 ORF. A plasmid with a frameshift mutation at this NaeI site, pUC19HybIFS, was produced by digesting pUC19HybI with NgoAIV (an isoschizomer of NaeI which produces cohesive ends), blunt-ending the overhanging ends with mung bean nuclease, and relegating the blunt ends to produce a four base pair deletion that destroys the NaeI site and disrupts the 603 ORF reading frame. This frameshift, which was confirmed by dideoxynucleotide sequencing (United States Biochemical Corp. Sequenase kit, Cleveland, Ohio), was predicted, on the basis of the published L-1 DNA sequence of AcMNPV (Possee et al. [1991] *Virology* 185:229–241), to cause premature termination of 603 ORF translation at a site fourteen amino acids downstream of the deletion. Plasmids were sequenced in both directions with the aid of synthetic oligonucleotide primers which provided sufficient overlap between contiguous sequences for confident alignments and unambiguous sequence information. The sequence was deposited in the EMBL/GenBank data libraries under accession number AFO25997.

Amino acid sequences can be aligned using the Pileup programs from Wisconsin package (version 8.0, Tenetics Computer Group, 1994), and comparisons can be displayed using the Boxshade program, version 2.7, contributed to the public domain by Kay Hofmann.

Example 3

Virus Bioassays

The $LC_{50}$ (concentration of occluded viruses required to kill 50% of the test larvae) and $ET_{50}$ (mean time to effectively kill or paralyze 50% of the test larvae) for V-8 and L-1 were determined by the diet incorporation method using *Spodoptera frugiperda* (J. E. Smith) and *Trichoplusia ni* (Hübner) neonates as previously described (U.S. Pat. No. 5,266,317). The toxin-expressing viruses, vV8EGTdel, and V-8 were also tested on *S. frugiperda* by the diet incorporation method. Five virus concentrations were tested using 60 insects per dose per virus. Paralysis or death was monitored every 8 hours.

The $LC_{50}$ and $ET_{50}$ of two independent L-1 revertant and two 603 frameshift virus isolates were determined by droplet feeding assays using neonate *S. frugiperda* I (Popham et al. [1997] *Biol. Control* 10:83–91). The V-8 virus was included in the bioassays in duplicate. Five virus concentrations with 30 insects per dose were tested for each virus, and larvae were monitored every six hours. $LC_{50}$s were determined using Polo-PC (Robertson and Prieler, [1992] *Pesticide Bioassays with Arthropods*, CRC Press, Boca Raton, Fla.) and $ET_{50}$s were determined by the Vistat 2.1 program (Hughes [1990] *Vistat. Statistical Package for the Analysis of Baculovirus Bioassay Data*, Boyce Thompson Institute at Cornell University, Ithaca, N.Y.).

Polyhedral inclusion bodies (PIBs) of L-1, V-8, vEcoRIHybI, and vEcoRIHybIFS or other genetically modified viruses were prepared simultaneously from infected *Trichoplusia ni* larvae as previously described (O'Reilly et al. [1992] supra). $LC_{50}$ data (the concentration of virus (PIBs/ml of diet) required for one half of the larvae to die by ten days post infection) and $LT_{50}$ data (the time taken, at a specific viral concentration, for one half of the larvae to die) were collected from neonate bioassays performed on *Spodoptera frugiperda* larvae. Neonates were allowed to feed for 24 hours on diet containing various concentrations of PIBs from the viruses being assayed and then transferred to individual cups containing diet without virus. The seven doses of each virus assayed were $5\times10^4$, $2\times10^5$, $5\times10^5$, $1\times10^6$, $2\times10^6$, $5\times10^6$, and $2\times10^7$ PIBs/ml. Sixty larvae were assayed per dose. Larval mortality was recorded at 48, 72, 84, 90, 96, 102, 108, 120, 132, and 144 hours post infection (p.i.). A final mortality count was performed at ten days post infection. $LT_{50}$ and $LC_{50}$ values were determined using probit analysis (Daum [1970] *Bulletin of the Entomological Soc. of America* 16:10–15).

Alternate virulence testing was done as follows: Trays were purchased from C-D International, Inc., and contained 32 separate arenas per tray. Each 4×4 cm (16 cm²) arena contained 5 ml of appropriate artificial diet. Clear vented adhesive tops from C-D International, Inc., enclosed the insect in the arena following treatment and infestation. These clear tops allowed for easy scoring. The surface of the Stoneville (soybean/wheat germ diet) or pinto bean (Bio-Serv, Inc., Frenchtown, N.J., Diet #9393) diet was contaminated with 0.4 ml of aqueous viral solution. The dilutions ranged from $1\times10^8$ to $1\times10^1$ PIBs/ml, in 10-fold dilutions, depending upon the insect species tested. The applications were evenly distributed by rotating the tray and solutions were allowed to dry in a laminar flow hood. Bioassay trays were held at 28° C. in continuous fluorescent light throughout the study period. Readings were taken twice a day to observe early onset time of infection. $LC_{50}$ values were calculated from the BASIC log/probit statistics package and based on mortality versus dose at 8 days post-treatment. The To (time at 0 hours) was based on initial average time when the larva was exposed to the treated diet. The $LT_{50}$ value was calculated from the BASIC log/probit statistics package based on mortality versus hours. The $LT_{50}$ data calculated were derived from the $LD_{95}$ value (based on a dose that was preferably less than 2 logs greater than the $LC_{50}$ value).

Example 4
Recombinant Virus Construction

Recombinant viruses are prepared essentially as described in O'Reilly et al. (1992) supra. The recombinant viruses vEcoRIHybI and vEcoRIHybIFS were constructed by cotransfecting SF-21 cells with vSynVI⁻gal DNA (Wang et al. [1991] *Gene* 100:131–137) and either pUC 19HybI plasmid DNA (for vEcoRIHybI) or pUC19HybIFS plasmid DNA (for vEcoRIHybIFs) (See Example 2). The virus vSynVI⁻gal expresses the *E. coli* lacZ gene instead of the polyhedrin gene and forms occlusion negative (OCC⁻), blue plaques in the presence of the chromogenic β-galactosidase indicator X-gal. Both pUC19HybI and pUC19HybIFS contain a polyhedrin gene; thus recombination between plasmid DNA derived from the polyhedrin region and viral DNA produced white occlusion positive (OCC⁺) viral plaques. Viruses forming white OCC⁺ plaques have lost the lacZ gene and acquired a functional polyhedrin gene through allelic replacement.

To create an L-1 derivative with a truncated ORF 603 product, pUC9I-I+ was digested with NgoAIV, which cleaves once within ORF 603, and then treated with mung bean nuclease. The resulting blunt ends were religated to form pUC19I-IFS+. Sequencing confirmed the introduction of a frameshift which is predicted to cause premature termination during ORF 603 translation at a site fourteen amino acids downstream of the former NgoAIV site. Plasmids pUC19I-I+ and pUC19I-IFS+ were individually cotransfected with vSynVI⁻gal (Wang et al. [1991] supra) to construct a revertant equivalent to L-1 and a 603 frameshift mutant, respectively. Recombinant viruses were generated by allelic replacement (O'Reilly et al. [1992] supra) and were selected based on their white, occlusion-positive, plaque phenotype. Each recombinant virus was verified by restriction enzyme analysis.

Viruses, vV8EEHSPtox34SB and vV8EEp6.9tox34B (FIG. 4B), were created in a series of steps as follows. V-8 DNA was cotransfected with the plasmid, pEGTZ (O'Reilly and Miller [1990]) to construct a V-8-based virus, vVail8Z, with a *Escherichia coli* lacZ gene inserted into egt. vVail8Z DNA was then cotransfected with the plasmid pEGTdel (O'Reilly and Miller [1991]) to construct a virus, vV8EGTdel, with a deletion in egt. A double-stranded oligonucleotide was constructed by annealing the following complementary oligonucleotides together AGC TTC CTG CAG GAC TAG TCC CGG CAA TTC CCT GAG GT (SEQ ID NO:11) and CTA GAC CTC AGG GAA TTC CCG GGA CTA GTC CTG CAG GA (SEQ ID NO:12). The resulting oligonucleotide had cohesive HindIII and XbaI ends and internal Sse8387I, SpeI, SmaI, EcoRI, and Bsu36I sites, and was ligated to the vector Bluescript KS II+ previously digested with XbaI and HindIII to create the plasmid pBSSseBsu. An hsp70-promoted lacZ cassette was released by BamHI from pHS70lacZ (Lu and Miller [1996] *J. Virol.* 70:5123–5130), the ends filled in with the large fragment of DNA polymerase I, and the resulting cassette ligated into the SmaI site of pBSSseBsu to generate pHSPlacZSseBsu. Plasmid pPMD207 contained the V-8 EcoRI-I fragment cloned into the EcoRI site of Bluescript II KS– with unique Sse8837I and Bsu36I sites inserted 92 nucleotides upstream of the polh ORF, equivalent to nucleotide #4427 of the C6 variant of AcMNPV (Ayres et al. [1994] supra). pPMD207 and PHSPlacZSseBsu were subsequently digested with Sse8387I and Bsu36I, and the HSP70lacZ fragment was ligated into pPMD207 to form pV8EcoRIlacZ. The virus, vV8EGTdel, was allelically recombined with pV8EcoRIlacZ to create an EGT deleted virus with lacZ inserted upstream of polh and flanked by Sse837I and Bsu36I sites.

Plasmid p6.9tox34SseBsu was constructed by digesting pBSSseBsu with SmaI and EcoRI. The plasmid pSP-p6.9tox34 (Lu et al. [1996] supra) was digested with EcoRV and EcoRI and the p6.9-promoted tox34 fragment was gel isolated and ligated into the digested pBSSseBsu. To create the plasmid pHSPtoxSseBsu, first pHSPtox34 was generated by digesting PHspGUSunilink (Popham et al. [1997] supra) and pHSP70PLVI⁺tox34 (McNitt et al. [1995] supra) with BglII and PstI. The tox34 fragment was then ligated into the Bluescript vector downstream of the HSP70 promoter. Subsequently, pHSPtox34 was digested with PstI the ends filled in with the large fragment of DNA polymerase I and digested with SpeI. Plasmid pHSPtox34SseBsu was constructed by digesting pBSSseBsu with SmaI and SpeI, and the released HSP70-promoted tox34 cassette was ligated into the corresponding sites. Plasmids p6.9tox34SseBsu and PHSPtox34SseBsu were digested with Sse837I and Bsu36I, and the resulting tox34 containing DNA fragments were gel isolated. vV8EGTEcoRIlacZ DNA was then digested with Sse837I and BsuI, and ligated to each tox34 fragment. The ligation products were transfected into SF21 cells. White plaques were purified, the resulting viruses were amplified, and their identities were verified by restriction enzyme analysis.

Example 5
Field Testing of Variant Baculovirus

The field trial program evaluates the efficacy of V8vEGTDEL relative to AcMNPV wild-type against important lepidopteran pests which attack vegetables. Pest organisms targeted in these field trials include cabbage looper, *Trichoplusia ni*; beet armyworm, *Spodoptera exigua*; fall armyworm, *Spodoptera frugiperda*; southern armyworm, *Spodoptera eridania*; tobacco budworm, *Heliothis virescens*; corn earworm, *Helicoverpa zea*, diamondback moth, *Plutella xylostella*; cabbageworm, *Pieris rapae*. Each test is conducted on land currently used for growth/production of row crops (i.e., commercial or research farms). The crop used in each test is a leafy vegetable (e.g., lettuce) or a crucifer (e.g., cabbage). Each field trial consists of the following eight treatments: V8vEGTDEL (see Examples 6 and 7 hereinbelow) at $1\times10^9$, $10^{11}$, and $10^{13}$ PIBs/acre; AcMNPV at $1\times10^9$, $10^{11}$, and $10^{13}$ PIBs/acre, and untreated control. Within a given test, each treatment will be applied to the crop no more than six (6) times; treatments will be applied on an "as needed" basis (i.e., as pest populations warrant, probably 5- to 14-day intervals).

Within each test, there is a maximum of six applications of each treatment. Treatments are applied to plots in each test by using ground equipment, either small tractor sprayers or $CO_2$-driven backpack sprayers. Treatments are diluted in water and applied through standard agricultural hydraulic spray booms and nozzles. The maximum size of a treatment plot (i.e., replicate) in each test is 0.018 acres (i.e., 4 rows wide×60 ft. long, row spacing of 40 in.). The maximum number of plots (i.e., replicates) per treatment in each test is four. Each test is monitored on at least a weekly basis for the duration of the study. Each of these trials will be conducted on secured private farm land or research farms (no trespassing by unauthorized individuals). At the conclusion of each test, the test area and a 10 ft.-wide untreated test perimeter undergo "crop destruction" (i.e., rather than being harvested for commercial use, the treated and adjacent crop is shredded and plowed underground).

Soil is perhaps the most important reservoir for persistence of virus in the environment. The monitoring program consists of the collection of 4 soil samples (each 7.6 cm in depth) totaling 500 g from within the test site and from an area 100 ft outside the treatment zone. Samples are taken approximately midway through the test. A second set of samples are collected at the end of the test after all disinfection procedures (as described below) have been completed.

Monitoring for viable, infectious virus is important because immunodetection and PCR methods make no distinction between infectious occlusion bodies and non-viable remnants of viral particles. The only reliable method for determining if viable, infectious viral particles are present in the soil samples is to perform bioassays of the samples on a highly susceptible insect host such as *Heliothis virescens*. From each 500 g sample of soil, 25 g is used in the bioassay. A standard method for isolation of viral occlusion bodies from soil is used. This method efficiently recovers approximately 46% of polyhedra from soil. The $LC_{50}$ for AcMNPV in our standard diet overlay assay is 300–1000 polyhedra/ arena for *H. virescens*. Therefore, if each larvae to be bioassayed is fed the isolate from 1 g of soil this assay reliably detects 600–2000 viral occlusion bodies per gram of assayed soil. Larvae which exhibit typical symptoms of viral infection in the bioassay are examined for the presence of occlusion bodies using light microscopy. If polyhedra are observed, they are isolated from the cadaver for DNA isolation from the occlusion bodies and a standard PCT assay (routinely performed in the lab) is done using primers flanking the vEGTDEL deletion (See FIG. 6, e.g.). The efficiency of DNA recovery and the PCR assay approaches 100%. If the virus present is vEGTDEL, then a DNA fragment of a characteristic size is observed, allowing unambiguous identification of the virus as vEGTDEL. Other viruses generate DNA fragments of differing sizes.

AcMNPV variants having deletions in the egt gene can arise spontaneously in nature, and such viruses are subject to a severe replicative disadvantage that will not allow them to compete effectively with indigenous viruses in the environment. Furthermore, since egt-inactivated virus produce 30%–50% fewer polyhedra following a successful infection, environmental persistence is further compromised. Contaminated plants within the test site and 10 ft.-wide buffer, tools, and farm implements are topically sterilized with a 1% bleach wash to prevent unnecessary dispersal of the viral insecticide.

The V8vEGTDEL formulation for the field trial program is in the form of a wettable powder. On a weight:weight basis, ingredients of this formulation are as follows:

|  | % Weight |
|---|---|
| V8vEGTDEL | 10.00 |
| EUDRAGIT S10 | 0.45 |
| UV-9 oxybenzone | 2.50 |
| polyethylene glycol MW400 | 0.10 |
| MIRASPERSE | 39.10 |
| REAX ATN lignin sulfonate | 4.90 |
| 10X Sugar | 19.45 |
| MOREWET EFW | 19.60 |
| MICROCEL E | 3.90 |
|  | 100.00 |

EUDRAGIT S100 (Rohm Pharma Co.) comprises methyl methacrylic and methyl methacrylate. It is a pH dependent coating agent which holds UV9 on the PIBs, and it slightly prolongs photostability of the formulation. UV-9 oxybenzone (Cytech Ind.) also provides slight photostability to the formulation. Polyethylene glycol MW400 (Aldrich Chemical Co.) provides flexibility to the UV-protectant coatings. MIRASPERSE (Staley Co.) is a starch-based "sticker", and provides rainfastness to the formulation after it is applied to the crop. REAX ATN (West Waco Co.) is a lignin sulfonate, and it is used as a dispersant and keeps the particles separate in the liquid phase (i.e., in the water diluent). Sugar is used as an insect feeding stimulant and/or attractant. MOREWET EFW (Witco Co.) is a wetting agent, so that the formulation can more effectively spread across the surface of a treated leaf. MICROCEL E (World Minerals, Lampoc, Calif.) is a clay-based flow agent that prevents the wettable powder from caking during storage.

For use in the test formulations, the PIBs (polyhedrin inclusion bodies) are air-milled to under 10 $\mu$m in size, and coated with an organic solution containing EUDRAGIT S 100, UV-9, and MW400. The other aforementioned inerts are blended and Fitz-milled to make a pre-blend. The coated PIBs and the pre-blend are blended together and Fitz-milled, and then the formulation is packaged. No extraneous microorganisms will be present in the formulation since production in tissue culture requires the use of sterile procedures. In each 10 g of wettable powder formulation, there is 1 g ($2\times10^{11}$ PIBs) of V8vEGTDEL.

A preferred wettable powder insecticidal composition is as follows:

| Ingredient | Nominal Percent (w/w) |
|---|---|
| V8vEGTDEL polyhedrin inclusion bodies | 10.0% |
| MORWET D425 | 30.0% |
| MOREWET EFW | 20.0% |
| Kaolin Clay | 16.0% |
| MICROCEL | 16.0% |
| UV-9 oxybenzone or charco | 5.0% |
| EUDRAGIT S100 | 2.0% |
| Citric Acid | 0.9% |
| polyethylene glycol MW400 | 0.1% |

The active ingredient is V8vEGTDEL. MOREWET D425 is used as a dispersant and keeps the particles separate in the liquid phase (i.e., in the water diluent). MOREWET EFW (Witco Co.) is a wetting agent, so that the formulation can more effectively spread across the surface of a treated leaf. Kaolin Clay is a bulking agent. MICROCEL E (World Minerals, Lampoc, Calif.) is a flow agent that prevents the wettable powder from caking. UV-9 (or charcoal) provides slight photostability to the formulation. EUDRAGIT S 100 (Rohm Pharma Co.) also slightly prolongs photostability of the formulation. Citric acid is used for pH adjustment. MW400 (Aldrich Chemical Co.) provides flexibility to the UV-protectant coatings.

A stilbene brightener is optionally added (at approximately 5% w/w) to PIBs in alternative preferred wettable powder formulations, and the percentages of other inert ingredients are then adjusted accordingly. Stilbenes provide some protection against UV inactivation and can also serve to enhance or potentiate virus infectivity, particularly in insects which are less susceptible to the insect virus, see, e.g., U.S. Pat. No. 5,246,936 (issued Sep. 21, 1993, Treacy et al.), which is incorporated by reference herein.

In this formulation the PIBs are first coated using an aqueous coating procedure. A 1% (w/v) suspension of EUDRAGIT S100 is prepared in water. The EUDRAGIT is dissolved by adjusting the pH to between 9.0 and 9.5. Viral PIBs, BLANKOPHOR BBH (stilbene brightner, Miles Inc; if used), and UV-9 oxybenzone or charcoal in the proper proportions are added. The mixture is blended to create an even suspension and then air-dried. The dried coated PIBs are then air-milled to achieve a small particle size. This material is then dry blended with the prescribed amounts of MOREWET 425, MOREWET EFW, Kaolin Clay, MICROCEL E, Citric acid and polyethylene glycol MW400 and then packaged as the final formulation. The preferred particle size of the blended material is less than 20 $\mu$m.

Example 6

EGT-deficient Virus Derivatives

The position of the egt gene on the AcMNPV genome is illustrated in FIG. 2B. A scale in map units is presented above the map of the AcMNPV genome in FIG. 1A. The nucleotide sequence of the AcMNPV L-1 egt gene and flanking regions has been determined (FIG. 6, SEQ ID NO:5). FIG. 1A shows a linear map of the AcMNPV L-1 genome after cleavage with restriction endonucleases EcoRI and HindIII. FIG. 1B is an enlargement of the AcMNPV genome from 7.6 to 11.1 map units showing the location of the egt gene. The AcMNPV strain L-1 has been described (Lee and Miller [1978] *J. Virol.* 27:754). Cloned L-1 DNA fragments and the names of the resultant plasmids are shown in FIG. 1C. Fragment 1, which extends from the PstI site at 7.6 mu to a BamHI site at 11.1 mu, is cloned into the plasmid vector pUC19; fragments 2 and 3 (from PstI (7.6 mu) to EcoRI (8.65 mu) and from EcoRI (8.65 mu) to SalI (10.5 mu), respectively) are both cloned into the vectors BLUESCRIPT M13+ and BLUESCRIPT M13- (Stratagene, San Diego, Calif.). Fragment 5 BstEII (8.35 mu) to BstEII (8.7 mu) is cloned into BLUESCRIPT M13+.

The coding sequence of the egt gene is presented in SEQ ID NO:5 from nucleotide 149 to nucleotide 1669.

To construct V-8 AcMNPV recombinant viruses (e.g., V-8) incapable of expressing a functional egt gene, further manipulation of the plasmid clones described in Example I is required. Plasmid pUCBCPsB is cleaved with restriction endonucleases EcoRI and XbaI (see FIG. 5A for sites within the egt gene) and the small fragment is discarded. The *Escherichia coli* lacZ gene, excised from pSKS104 (Casadaban et al. [1983] *Methods Enzymol.* 100:293–303) with EcoRI and AhaIII, is then inserted between the EcoRI and XbaI sites after the XbaI overhanging ends are filled in using T4 DNA polymerase. The resultant plasmid is designated pEGTZ. In this plasmid, the inserted lacZ gene is in frame with the preceding egt coding sequences. Alternatively, the plasmid pEGTDEL is constructed by simply ligating the EcoRI and XbaI sites together (after both sites have been blunt-ended) without inserting any sequences between them.

Plasmid pEGTZ is then cotransfected with AcMNPV V-8 DNA into SF cells as described in Miller et al. (1986) supra. This procedure allows for homologous recombination to take place between sequences in the viral and plasmid DNAs, resulting in replacement of the viral egt gene with the egt-lacZ gene fusion from the plasmid. Because the remaining egt coding sequence is in frame with the lacZ sequences, such a recombinant virus will produce a fusion protein comprising the first 84 amino acids of egt joined to 13-galactosidase. The recombinant virus, termed vEGTZ, can be identified because β-galactosidase expression gives rise to blue viral plaques in the presence of a chromogenic indicator such as 5-bromo-4-chloro-3-indolyl-β-D-galactopyranoside (X-gal).

Recombinant virus V8vEGTDEL is obtained by cotransfecting the plasmid pEGTDEL and DNA from the virus vEGTZ into SF cells. Homologous recombination results in the replacement of the egt-lacZ fusion gene in V8vEGTZ with the deleted egt gene from pEGTDEL. The recombinant virus vEGTDEL is identified by its failure to form blue plaques in the presence of X-gal.

In a specific embodiment of an AcMNPV V-8 virus in which the egt is inactivated, a DNA fragment from 7.6–11.1 map units on the physical map of AcMNPV was cloned into a plasmid vector as described in U.S. Pat. No. 5,180,581, incorporated by reference herein.

This AcMNPV fragment contains the egt gene and flanking viral DNA. An internal deletion was made in the egt gene and the *E. coli* lacZ gene was fused in frame. The initial egt-deleted virus, designated vEGTZ, was constructed using this fusion plasmid to replace the egt gene in AcMNPV by allelic recombination mediated by cellular recombination mechanisms. Presence of a functional lacZ gene facilitated the identification of the recombinant virus by its blue color in plaque assays in the presence of an appropriate chromogenic indicator. An additional egt-deleted virus, vEGTDEL, was constructed by deleting an internal portion of the egt gene from the plasmid vector containing the 7.6–11.1 map unit region of the AcMNPV genome using PCR mediated mutagenesis. The sequence of the egt coding region and flanking sequences are shown in FIG. 6, along with the locations of the PCR primers. Deletion at the precise sites indicated in FIG. 3 results in the formation of two novel and easily characterized restriction enzyme sites (EcoRI and XhaI) at the deletion junction. This deletion plasmid was then used to replace the egt-deleted lac Z gene.

Example 7

EGT Assay

EGT enzymatic activity protein can be determined as follows: SF cells are infected with AcMNPV as described hereinbefore. Twelve hours post infection the cells and extracellular media are collected and processed separately. Uninfected cells are treated in parallel. Cell lysates or extracellular media are incubated in the presence of 1 mM UDP-glucose, UDP-galactose and 0.25 µCi($^3$H)ecdysone as described in O'Reilly and Miller (1989) *Science* 245:1110–1112. Ecdysteroid UDP-glucosyl transferase activity in the cell lysates or media catalyze the transfer of glucose from the UDP-glucose to ecdysone to form an ecdysone-glucose conjugate. Ecdysone and the ecdysone-sugar conjugate are separated from one another by silica gel thin layer chromatography (Bansal and Gessner [1988] *Anal. Biochem.* 109:321) and visualized by autoradiography. Ecdysone-glucose conjugates are only formed when wt AcMNPV-infected cell lysate or extracellular medium is assayed. No conjugates are observed when uninfected or egt-inactivated virus infected cell lysates or media are used, showing that the activity is due to egt expression. Most of the activity is located in the extracellular medium.

It should be understood that the foregoing relates only to preferred specific embodiments of the present invention and that numerous modifications or alterations may be made therein without departing from the spirit and the scope of the invention as set forth in the appended claims.

We claim:

1. An insecticidal composition comprising an effective amount of an isolated and purified recombinant Nuclear Polyhedrosis Virus which has been genetically modified to inactivate an ORF 603 or ORF 603 homolog, wherein said ORF 603 or an ORF 603 homolog is present in the genome of said Nuclear Polyhedrosis Virus in nature, which recombinant Nuclear Polyhedrosis Virus effects faster killing for at least one insect pest as compared with an isogenic comparison Nuclear Polyhedrosis Virus which expresses ORF 603 or ORF 603 homolog, and a carrier.

2. The insecticidal composition of claim 1 wherein said baculovirus is *Autographa californica* nuclear polyhedrosis virus, *Anagrapha falcifera* nuclear polyhedrosis virus or *Rachiplusia ou* nuclear polyhedrosis virus.

3. The insecticidal composition of claim 1 wherein the recombinant Nuclear Polyhedrosis Virus has been further genetically modified to inactivate a gene encoding ecdysteroid UDP-glycosyltransferase.

4. A method for improving a Nuclear Polyhedrosis Virus as an insect control agent, said method comprising the steps of (a) isolating a DNA segment of a Nuclear Polyhedrosis Virus, wherein the segment comprises at least part of an ORF 603 or an ORF 603 homolog;

(b) genetically modifying the DNA segment of step (a) to inactivate the ORF 603 or ORF 603 homolog; and (c) preparing a recombinant Nuclear Polyhedrosis Virus containing the genetically modified DNA segment of step (b), whereby a recombinant Nuclear Polyhedrosis Virus genetically modified to inactivate an ORF 603 or ORF 603 homolog is produced, with the result that the Nuclear Polyhedrosis Virus is improved as an insect control agent due to the virulence of the recombinant, genetically modified Nuclear Polyhedrosis Virus being increased for at least one insect in comparison to that of the Nuclear Polyhedrosis Virus which has not been so genetically modified.

5. The method of claim 4 wherein said Nuclear Polyhedrosis Virus is *Anagrapha falcifera* NPV, *Rachiplusia ou* NPV, *Lymantria dispar* NPV, *Autographa californica* NPV, *Synographa falcifera* NPV, *Spodoptera lituralis* NPV, *Spodoptera exigua* NPV, *Spodoptera frugiperda* NPV, *Heliothis armigera* NPV, *Mamestra brassicae* NPV, *Choristoneura fumiferana* NPV, *Trichoplusia ni* NPV, *Helicoverpa zea* NPV and *Manduca sexta* NPV.

* * * * *

UNITED STATES PATENT AND TRADEMARK OFFICE
CERTIFICATE OF CORRECTION

PATENT NO. : 6,156,309
DATED : December 5, 2000
INVENTOR(S) : Miller et al.

It is certified that error appears in the above-identified patent and that said Letters Patent is hereby corrected as shown below:

Column 2,
Line 4, insert a period following "crops".

Column 5,
Line 58, delete "represents" and replace with -- represent --.

Column 6,
Line 10, delete "Nael" and replace with -- NaeI --.
Line 23, please insert a comma following "L-1" and following "lef-2".

Column 7,
Line 28, insert -- lack the -- between "all" and "appooximately".

Column 10,
Line 24, delete "AFNPV" and replace with -- AfNPV --.

Column 18,
Table 4, footnote 2 delete "$10^{E}9$" and replace with -- $10^9$ --.

Column 22,
Line 17 and 23, delete "Nael" and replace with -- NaeI --.
Line 22, delete "relagating" and replace with -- religating --.
Line 38, delete "Tenetics" and replace with -- Genetics --.

Column 23,
Line 41, delete "To" and replace with -- $T_0$ --.
Line 67, delete "pUC9I-I+" and replace with -- pUC19I-I+ --.

UNITED STATES PATENT AND TRADEMARK OFFICE
CERTIFICATE OF CORRECTION

PATENT NO. : 6,156,309
DATED : December 5, 2000
INVENTOR(S) : Miller et al.

It is certified that error appears in the above-identified patent and that said Letters Patent is hereby corrected as shown below:

Column 24,
Line 55, delete "PhspGUSunilink" and replace with -- pHspGUSunilink --.

Column 46,
Last line of claim 5, delete "and" and replace with -- or --.

Signed and Sealed this

Second Day of October, 2001

Attest:

NICHOLAS P. GODICI
Attesting Officer
Acting Director of the United States Patent and Trademark Office

SEQUENCE LISTING

<160> NUMBER OF SEQ ID NOS: 12

<210> SEQ ID NO 1
<211> LENGTH: 1721
<212> TYPE: DNA
<213> ORGANISM: Autographa californica nucleopolyhedrovirus
<220> FEATURE:
<221> NAME/KEY: CDS
<222> LOCATION: (194)..(823)

<400> SEQUENCE: 1

```
acgcgttccg gcacgagctt tgattgtaat aagtttttac gaagcgatga catgaccccc      60
gtagtgacaa cgatcacgcc caaaagaact gccgactaca aaattaccga gtatgtcggt     120
gacgttaaaa ctattaagcc atccaatcga ccgttagtcg aatcaggacc gctggtgcga     180
gaagccgcga agt atg gcg aat gca tcg tat aac gtg tgg agt ccg ctc       229
            Met Ala Asn Ala Ser Tyr Asn Val Trp Ser Pro Leu
              1               5                  10 att aga gcg tca tgt tta gac aag aaa gct aca tat tta att gat ccc      277
Ile Arg Ala Ser Cys Leu Asp Lys Lys Ala Thr Tyr Leu Ile Asp Pro
         15                  20                  25 gat gat ttt att gat aaa ttg acc cta act cca tac acg gta ttc tac      325
Asp Asp Phe Ile Asp Lys Leu Thr Leu Thr Pro Tyr Thr Val Phe Tyr
     30                  35                  40 aat ggc ggg gtt ttg gtc aaa att tcc gga ctg cga ttg tac atg ctg      373
Asn Gly Gly Val Leu Val Lys Ile Ser Gly Leu Arg Leu Tyr Met Leu
 45                  50                  55                  60 tta acg gct ccg ccc act att aat gaa att aaa aat tcc aat ttt aaa      421
Leu Thr Ala Pro Pro Thr Ile Asn Glu Ile Lys Asn Ser Asn Phe Lys
                 65                  70                  75 aaa cgc agc aag aga aac att tgt atg aaa gaa tgc gta gaa gga aag      469
Lys Arg Ser Lys Arg Asn Ile Cys Met Lys Glu Cys Val Glu Gly Lys
             80                  85                  90 aaa aat gtc gtc gac atg ctg aac aac aag att aat atg cct ccg tgt      517
Lys Asn Val Val Asp Met Leu Asn Asn Lys Ile Asn Met Pro Pro Cys
         95                 100                 105 ata aaa aaa ata ttg aac gat ttg aaa gaa aac aat gta ccg cgc ggc      565
Ile Lys Lys Ile Leu Asn Asp Leu Lys Glu Asn Asn Val Pro Arg Gly
    110                 115                 120 ggt atg tac agg aag agg ttt ata cta aac tgt tac att gca aac gtg      613
```

```
Gly Met Tyr Arg Lys Arg Phe Ile Leu Asn Cys Tyr Ile Ala Asn Val
125                 130                 135                 140 gtt tcg tgt gcc aag tgt gaa aac cga tgt tta atc aag gct ctg acg        661
Val Ser Cys Ala Lys Cys Glu Asn Arg Cys Leu Ile Lys Ala Leu Thr
                145                 150                 155 cat ttc tac aac cac gac tcc aag tgt gtg ggt gaa gtc atg cat ctt        709
His Phe Tyr Asn His Asp Ser Lys Cys Val Gly Glu Val Met His Leu
                160                 165                 170 tta atc aaa tcc caa gat gtg tat aaa cca cca aac tgc caa aaa atg        757
Leu Ile Lys Ser Gln Asp Val Tyr Lys Pro Pro Asn Cys Gln Lys Met
            175                 180                 185 aaa act gtc gac aag ctc tgt ccg ttt gct ggc aac tgc aag ggt ctc        805
Lys Thr Val Asp Lys Leu Cys Pro Phe Ala Gly Asn Cys Lys Gly Leu
        190                 195                 200 aat cct att tgt aat tat tgaataataa aacaattata aatgctaaat               853
Asn Pro Ile Cys Asn Tyr
205             210 ttgtttttta ttaacgatac aaaccaaacg caacaagaac atttgtagta ttatctataa      913
ttgaaaacgc gtagttataa tcgctgaggt aatatttaaa atcatttca aatgattcac      973 agttaatttg cgacaatata attttatttt cacataaact agacgccttg tcgtcttctt     1033
cttcgtattc cttctctttt tcattttct cctcataaaa attaacatag ttattatcgt      1093
atccatatat gtatctatcg tatagagtaa attttttgtt gtcataaata tatatgtctt     1153
ttttaatggg gtgtatagta ccgctgcgca tagtttttct gtaatttaca acagtgctat     1213
tttctggtag ttcttcggag tgtgttgctt taattattaa atttatataa tcaatgaatt     1273
tgggatcgtc ggttttgtac aatatgttgc cggcatagta cgcagcttct tctagttcaa     1333
ttacaccatt ttttagcagc accggattaa cataactttc caaaatgttg tacgaaccgt     1393
taaacaaaaa cagttcacct ccctttttcta tactattgtc tgcgagcagt tgtttgttgt    1453
taaaaataac agccattgta atgagacgca caaactaata tcacaaactg gaaatgtcta    1513
tcaatatata gttgctgata tcatggagat aattaaaatg ataaccatct cgcaaataaa    1573
taagtatttt actgttttcg taacagtttt gtaataaaaa aacctataaa tatgccggat    1633
tattcatacc gtcccaccat cgggcgtacc tacgtgtacg acaacaagta ctacaaaaat    1693
ttaggtgccg ttatcaagaa cgctaagc                                        1721

<210> SEQ ID NO 2
<211> LENGTH: 210
<212> TYPE: PRT
<213> ORGANISM: Autographa californica nucleopolyhedrovirus

<400> SEQUENCE: 2

Met Ala Asn Ala Ser Tyr Asn Val Trp Ser Pro Leu Ile Arg Ala Ser
1               5                   10                  15

Cys Leu Asp Lys Lys Ala Thr Tyr Leu Ile Asp Pro Asp Phe Ile
                20                  25                  30

Asp Lys Leu Thr Leu Thr Pro Tyr Thr Val Phe Tyr Asn Gly Gly Val
            35                  40                  45

Leu Val Lys Ile Ser Gly Leu Arg Leu Tyr Met Leu Leu Thr Ala Pro
        50                  55                  60

Pro Thr Ile Asn Glu Ile Lys Asn Ser Asn Phe Lys Lys Arg Ser Lys
65                  70                  75                  80

Arg Asn Ile Cys Met Lys Glu Cys Val Glu Gly Lys Lys Asn Val Val
                85                  90                  95
```

```
Asp Met Leu Asn Asn Lys Ile Asn Met Pro Pro Cys Ile Lys Lys Ile
            100                 105                 110

Leu Asn Asp Leu Lys Glu Asn Asn Val Pro Arg Gly Gly Met Tyr Arg
        115                 120                 125

Lys Arg Phe Ile Leu Asn Cys Tyr Ile Ala Asn Val Val Ser Cys Ala
    130                 135                 140

Lys Cys Glu Asn Arg Cys Leu Ile Lys Ala Leu Thr His Phe Tyr Asn
145                 150                 155                 160

His Asp Ser Lys Cys Val Gly Glu Val Met His Leu Leu Ile Lys Ser
                165                 170                 175

Gln Asp Val Tyr Lys Pro Pro Asn Cys Gln Lys Met Lys Thr Val Asp
            180                 185                 190

Lys Leu Cys Pro Phe Ala Gly Asn Cys Lys Gly Leu Asn Pro Ile Cys
        195                 200                 205

Asn Tyr
    210

<210> SEQ ID NO 3
<211> LENGTH: 1763
<212> TYPE: DNA
<213> ORGANISM: Autographa californica nucleopolyhedrovirus
<220> FEATURE:
<221> NAME/KEY: CDS
<222> LOCATION: (194)..(823)

<400> SEQUENCE: 3
acgcgttccg gcacgagctt tgattgtaat aagttttac gaagcgatga catgaccccc      60
gtagtgacaa cgatcacgcc caaaagaact gccgactaca aaattaccga gtatgtcggt    120
gacgttaaaa ctattaagcc atccaatcga ccgttagtcg aatcaggacc gctggtgcga    180
gaagccgcga agt atg gcg aat gca tcg tat aac gtg tgg agt ccg ctc       229
            Met Ala Asn Ala Ser Tyr Asn Val Trp Ser Pro Leu
              1               5                  10 att agc gcg tca tgt tta gac aag aaa gct aca tat tta att gat ccc      277
Ile Ser Ala Ser Cys Leu Asp Lys Lys Ala Thr Tyr Leu Ile Asp Pro
         15                 20                  25 gat gat ttt att gat aaa ttg acc cta act cca tac acg gta ttc tac      325
Asp Asp Phe Ile Asp Lys Leu Thr Leu Thr Pro Tyr Thr Val Phe Tyr
 30                  35                  40 aat ggc ggg gtt ttg gtc aaa att tcc gga ctg cga ttg tac atg ctg      373
Asn Gly Gly Val Leu Val Lys Ile Ser Gly Leu Arg Leu Tyr Met Leu
 45                  50                  55                  60 tta acg gct ccg ccc act att aat gaa att aaa aat tcc aat ttt aaa      421
Leu Thr Ala Pro Pro Thr Ile Asn Glu Ile Lys Asn Ser Asn Phe Lys
                 65                  70                  75 aaa cgc agc aag aga aac att tgt atg aaa gaa tgc gca gaa gga aag      469
Lys Arg Ser Lys Arg Asn Ile Cys Met Lys Glu Cys Ala Glu Gly Lys
             80                  85                  90 aaa aat gtc gtt gac atg ctg aac agc aag atc aat atg cct ccg tgt      517
Lys Asn Val Val Asp Met Leu Asn Ser Lys Ile Asn Met Pro Pro Cys
         95                 100                 105 ata aaa aaa ata ttg ggc gat ttg aaa gaa aac aat gta cca cgc ggc      565
Ile Lys Lys Ile Leu Gly Asp Leu Lys Glu Asn Asn Val Pro Arg Gly
110                 115                 120 ggt atg tac agg aag aga ttt ata tta aac tgt tac att gca aac gtg      613
Gly Met Tyr Arg Lys Arg Phe Ile Leu Asn Cys Tyr Ile Ala Asn Val
125                 130                 135                 140 gtt tcg tgt gcc aaa tgt gaa aac cga tgt tta atc aat gct ctg acg      661
Val Ser Cys Ala Lys Cys Glu Asn Arg Cys Leu Ile Asn Ala Leu Thr
```

```
                    145                  150                    155
cat ttc tac aac cac gat tcc aaa tgt gtg ggt gaa gtc atg cat ctt    709
His Phe Tyr Asn His Asp Ser Lys Cys Val Gly Glu Val Met His Leu
                160                 165                 170 tta att aaa tcc caa gat gtt tat aaa cca cca aac tgc caa aaa atg    757
Leu Ile Lys Ser Gln Asp Val Tyr Lys Pro Pro Asn Cys Gln Lys Met
            175                 180                 185 aaa aat gtc gac aag ctt tgc ccg ttt gct ggc aac tgc aag ggt ctc    805
Lys Asn Val Asp Lys Leu Cys Pro Phe Ala Gly Asn Cys Lys Gly Leu
        190                 195                 200 aat cct att tgt aat tat tgaataataa aacaattata aatgctaaat           853
Asn Pro Ile Cys Asn Tyr
205             210 ttgttttta ttaacgatac aaaccaaacg caacaagaac atttgtagaa ttatctataa    913
ttgaaaacgc ataattataa tcgtcaaggt aatgtttaaa atcattttca atgattcac    973 agttaatttg cgacagtata attttgtttt cacataaact agacgccttt atctgtctgt  1033
cgtcttcttc gtattctttt tctttttcat ttttctcttc ataaaaattc acataattat  1093
tatcgtatcc atatatgtat ctgtcgtaaa gagtaaattt tttgttgtca taaatatata  1153
tgtctttttt aatggggtgt atagtaccgc tgcgcatagt ttttctttaa tttaaaccag  1213
tgctattttc tggtaattct tcggagtgtg ttgctttaat tattaaattt atataatcaa  1273
tgaatttggg atcgtcggtt ttgtacaata tgttgccggc atagtacgca gctggctcta  1333
aatcaatatt ttttaaacaa cgactggatc aacattacca ttttttagca acactggatt  1393
aacataattt tccaaaatgc tgtacgaagc gtttaacaaa aacagttcac ctccgttttc  1453
tatactatcg tctgcgagca gttgcttgtt gttaaaaata acggccattg taatgaaacg  1513
cacaaactaa tattcacac taaaaaaatc tatcatttcg gcttaatata tagttgctga   1573
tattatgtaa ataattaaaa tgataaccat ctcgcaaata aataagtatt ttactgtttt  1633
cgtaacagtt ttgtaataaa aaaacctata aatatgccgg attattcata ccgtcccacc  1693
atcgggcgta cctacgtgta cgacaacaaa tattacaaaa atttaggtgc cgttatcaag  1753
aacgctaagc                                                         1763

<210> SEQ ID NO 4
<211> LENGTH: 210
<212> TYPE: PRT
<213> ORGANISM: Autographa californica nucleopolyhedrovirus

<400> SEQUENCE: 4

Met Ala Asn Ala Ser Tyr Asn Val Trp Ser Pro Leu Ile Ser Ala Ser
  1               5                  10                  15

Cys Leu Asp Lys Lys Ala Thr Tyr Leu Ile Asp Pro Asp Asp Phe Ile
             20                  25                  30

Asp Lys Leu Thr Leu Thr Pro Tyr Thr Val Phe Tyr Asn Gly Gly Val
         35                  40                  45

Leu Val Lys Ile Ser Gly Leu Arg Leu Tyr Met Leu Leu Thr Ala Pro
     50                  55                  60

Pro Thr Ile Asn Glu Ile Lys Asn Ser Asn Phe Lys Lys Arg Ser Lys
 65                  70                  75                  80

Arg Asn Ile Cys Met Lys Glu Cys Ala Glu Gly Lys Lys Asn Val Val
                 85                  90                  95

Asp Met Leu Asn Ser Lys Ile Asn Met Pro Pro Cys Ile Lys Lys Ile
            100                 105                 110
```

-continued

```
Leu Gly Asp Leu Lys Glu Asn Asn Val Pro Arg Gly Met Tyr Arg
        115                 120                 125
Lys Arg Phe Ile Leu Asn Cys Tyr Ile Ala Asn Val Val Ser Cys Ala
130                 135                 140
Lys Cys Glu Asn Arg Cys Leu Ile Asn Ala Leu Thr His Phe Tyr Asn
145                 150                 155                 160
His Asp Ser Lys Cys Val Gly Glu Val Met His Leu Leu Ile Lys Ser
                165                 170                 175
Gln Asp Val Tyr Lys Pro Pro Asn Cys Gln Lys Met Lys Asn Val Asp
            180                 185                 190
Lys Leu Cys Pro Phe Ala Gly Asn Cys Lys Gly Leu Asn Pro Ile Cys
        195                 200                 205
Asn Tyr
    210

<210> SEQ ID NO 5
<211> LENGTH: 2793
<212> TYPE: DNA
<213> ORGANISM: Autographa californica nucleopolyhedrovirus

<400> SEQUENCE: 5
gtcgacgcgc ttctgcgtat aattgcacac taacatgttg ccctttgaac ttgacctcga      60
ttgtgttaat ttttggctat aaaaaggtca ccctttaaaa tttgttacat aatcaaatta     120
ccagtacagt tattccggttt gaagcaaaat gactattctc tgctggcttg cactgctgtc     180
tacgcttact gctgtaaatg cggccaatat attggccgtg tttcctacgc cagcttacag     240
ccaccatata gtgtacaaag tgtatattga agcccttgcc gaaaaatgtc acaacgttac     300
ggtcgtcaag cccaaactgt tgcgtattc aactaaaact tattgcggta atatcacgga     360
aattaatgcc gacatgtctg ttgagcaata caaaaaacta gtggcgaatt cggcaatgtt     420
tagaaagcgc ggagtggtgt ccgatacaga cacggtaacc gccgctaact acctaggctt     480
gattgaaatg ttcaaagacc agtttgacaa tatcaacgtg cgcaatctca ttgccaacaa     540
ccagacgttt gatttagtcg tcgtggaagc gtttgccgat tatgcgttgg tgtttggtca     600
cttgtacgat ccggcgcccg taattcaaat cgcgcctggc tacggttttgg cggaaaactt     660 tgacacggtc ggcgccgtgg cgcggcaccc cgtccaccat cctaacattt ggcgcagcaa     720
tttcgacgac acggaggcaa acgtgatgac ggaaatgcgt ttgtataaag aatttaaaat     780
tttggccaac atgtccaacg cgttgctcaa acaacagttt ggacccaaca caccgacaat     840
tgaaaaacta cgcaacaagg tgcaattgct tttgctaaac ctgcatccca tatttgacaa     900
caaccgaccc gtgccgccca gcgtgcagta tcttggcgga ggaatccatc ttgtaaagag     960
cgcgccgttg accaaattaa gtccggtcat caacgcgcaa atgaacaagt caaaagcgg     1020 aacgatttac gtaagttttg ggtcgagcat tgacaccaaa tcgtttgcaa acgagtttct     1080
ttacatgtta atcaatacgt tcaaaacgtt ggataattac accatattat ggaaaattga     1140
cgacgaagta gtaaaaaaca taacgttgcc cgccaacgta atcacgcaaa attggtttaa     1200
tcaacgcgcc gtgctgcgtc ataaaaaaat ggcggcgttt attacgcaag cggactaca     1260 atcgagcgac gaggccttgg aagccgggat acccatggtg tgtctgccca tgatgggcga     1320 ccagtttac catgcgcaca aattacagca actcggcgta gcccgcgcct tggacactgt     1380
taccgtttcc agcgatcaac tactagtggc gataaacgac gtgttgttta acgcgcctac     1440
ctacaaaaaa cacatggccg agttatatgc gctcatcaat catgataaag caacgtttcc     1500
```

-continued

```
gcctctagat aaagccatca aattcacaga acgcgtaatt cgatatagac atgcatcag      1560 tcgtcaattg tattcattaa aaacaacagc tgccaatgta ccgtattcaa attactacat    1620
gtataaatct gtgttttcta ttgtaatgaa tcacttaaca cacttttaat tacgtcaata    1680
aatgttattc accattattt acctggtttt tttgagaggg gctttgtgcg actgcgcact    1740
tccagccttt ataaacgctc accaaccaaa gcaggtcatt attgtgccag gacgttcaaa    1800
ggcgaaacat cgaaatggag tctgttcaaa cgcgcttatg tgccagtagc aatcaatttg    1860
ctccgttcaa aaagcgccag cttgccgtgc cggtcggttc tgtgaacagt ttgacacaca    1920
ccatcacctc caccaccgtc accagcgtga ttccaaaaaa ttatcaagaa aaacgtcaga    1980
aaatatgcca cataatatct tcgttgcgta acacgcactt gaatttcaat aagatacagt    2040
ctgtacataa aaagaaactg cggcatttgc aaaatttgct aagaaaaaag aacgaaatta    2100
ttgccgagtt ggttagaaaa cttgaaagtg cacagaagaa gacaacgcac agaaatatta    2160
gtaaaccagc tcattggaaa tactttggag tagtcagatg tgacaacaca attcgcacaa    2220
ttattggcaa cgaaaagttt gtaaggagac gtttggccga gctgtgcaca ttgtacaacg    2280
ccgagtacgt gttttgccaa gcacgcgccg atggagacaa agatcgacag gcactagcga    2340
gtctgctgac ggcggcgttt ggttcgcgag tcatagtttta tgaaaatagt cgccggttcg    2400
agtttataaa tccggacgag attgctagtg gtaaacgttt aataattaaa catttgcaag    2460
atgaatctca aagtgatatt aacgcctatt aatttgaaag gtgaggaaga gcccaattgc    2520
gttgagcgca ttaccataat gccatgtatt ttaatagata ctgagatctg tttaaatgtc    2580
agatgccgtt ctccttttgc caaattcaaa gtattgatta ttgtagatgg ctttgatagc    2640
gcttatattc aggctacctt ttgtagcatt agcgatagtc taacaattgt taacaaatct    2700
aacgaaaagc atgtaacgtt tgacgggttt gtaaggccgg acgatgaagg tacaacaatg    2760
ccttatgtca ttggaccatt atattctgtc gac                                  2793
```

<210> SEQ ID NO 6  
<211> LENGTH: 341  
<212> TYPE: DNA  
<213> ORGANISM: Autographa californica nucleopolyhedrovirus

<400> SEQUENCE: 6

```
tgagacgcac aaactaatat cacaaactgg aaatgtctat caatatatag ttgctgatat     60
catggagata attaaaatga taaccatctc gcaaataaat aagtatttta ctgttttcgt    120
aacagttttg taataaaaaa acctataaat atgccggatt attcataccg tcccaccatc    180
gggcgtacct acgtgtacga caacaagtac tacaaaaatt taggtgccgt tatcaagaac    240
gctaagcgca agaagcactt cgccgaacat gagatcgaag aggctaccct cgaccccta    300 gacaactacc tagtggctga ggatccttc ctgggacccg g                          341
```

<210> SEQ ID NO 7  
<211> LENGTH: 351  
<212> TYPE: DNA  
<213> ORGANISM: Autographa californica nucleopolyhedrovirus

<400> SEQUENCE: 7

```
tgaaacgcac aaactaatat tacacactaa aaatgtctat catttcggct taatatatag     60
ttgctgatat tatgtaaata attaaaatga taaccatctc gcaaataaat aagtatttta    120
ctgttttcgt aacagttttg taataaaaaa acctataaat atgccggatt attcataccg    180
tcccaccatc gggcgtacct acgtgtacga caacaaatat tacaaaaatt taggtgccgt    240
```

```
tatcaagaac gctaagcgca agaagcactt cgccgaacat gagatcgaag aggctaccct        300 cgaccccta gacaactacc tagtggctga ggatcctttc ctgggacccg g                  351
```

<210> SEQ ID NO 8
<211> LENGTH: 351
<212> TYPE: DNA
<213> ORGANISM: Unknown
<220> FEATURE:
<223> OTHER INFORMATION: Description of Unknown Organism:baculovirus
      V1000
<220> FEATURE:
<223> OTHER INFORMATION: At all occurrences, "n" represents a
      nucleotide which has not been identified.

<400> SEQUENCE: 8

```
tgaaacgcac aaactaatat tacacactaa aaaaatctat catttcggct taatatatag        60
ttgctgatat tatgtaaata attaaaatga taaccatctc gcaaataaat aagtattta         120 ctgttttcgt aacagttttg taataaaaaa acctataaat atgccggatt attcataccg        180
tccgaccatc gggcgtacct acgtgtacga caacaaatat tacaaaaact tgggttctgt       240
tattaaaaac gccaagcgca agaagcacct aatcgaacat gaagaagagg agaagnactt       300 ggatcccta gacaattaca tggttgccnn agatccttt ctaggacctg g                  351
```

<210> SEQ ID NO 9
<211> LENGTH: 606
<212> TYPE: DNA
<213> ORGANISM: Autographa californica nucleopolyhedrovirus
<220> FEATURE:
<221> NAME/KEY: CDS
<222> LOCATION: (1)..(603)
<220> FEATURE:
<223> OTHER INFORMATION: Description of Artificial Sequence:
      oligonucleotide

<400> SEQUENCE: 9

```
atg gct gtt att ttt aac aac aaa caa ctg ctc gca gac aat agt ata        48
Met Ala Val Ile Phe Asn Asn Lys Gln Leu Leu Ala Asp Asn Ser Ile
1               5                   10                  15 gaa aag gga ggt gaa ctg ttt ttg ttt aac ggt tcg tac aac att ttg        96
Glu Lys Gly Gly Glu Leu Phe Leu Phe Asn Gly Ser Tyr Asn Ile Leu
            20                  25                  30 gaa agt tat gtt aat ccg gtg ctg cta aaa aat ggt gta att gaa cta       144
Glu Ser Tyr Val Asn Pro Val Leu Leu Lys Asn Gly Val Ile Glu Leu
        35                  40                  45 gaa gaa gct gcg tac tat gcc ggc aac ata ttg tac aaa acc gac gat       192
Glu Glu Ala Ala Tyr Tyr Ala Gly Asn Ile Leu Tyr Lys Thr Asp Asp
    50                  55                  60 ccc aaa ttc att gat tat ata aat tta ata att aaa gca aca cac tcc       240
Pro Lys Phe Ile Asp Tyr Ile Asn Leu Ile Ile Lys Ala Thr His Ser
65                  70                  75                  80 gaa gaa cta cca gaa aat agc act gtt gta aat tac aga aaa act atg       288
Glu Glu Leu Pro Glu Asn Ser Thr Val Val Asn Tyr Arg Lys Thr Met
                85                  90                  95 cgc agc ggt act ata cac ccc att aaa aaa gac ata tat att tat gac       336
Arg Ser Gly Thr Ile His Pro Ile Lys Lys Asp Ile Tyr Ile Tyr Asp
            100                 105                 110 aac aaa aaa ttt act cta tac gat aga tac ata tat gga tac gat aat       384
Asn Lys Lys Phe Thr Leu Tyr Asp Arg Tyr Ile Tyr Gly Tyr Asp Asn
        115                 120                 125 aac tat gtt aat ttt tat gag gac aaa aat gaa aaa gag aag gaa tac       432
Asn Tyr Val Asn Phe Tyr Glu Asp Lys Asn Glu Lys Glu Lys Glu Tyr
```

```
              130                 135                 140
gaa gaa gaa gac gac aag gcg tct agt tta aga gaa agt aaa att ata        480
Glu Glu Glu Asp Asp Lys Ala Ser Ser Leu Arg Glu Ser Lys Ile Ile
145                 150                 155                 160 ttg tcg caa att aac tgt gaa tca ttt gaa aat gat ttt aaa tat tac        528
Leu Ser Gln Ile Asn Cys Glu Ser Phe Glu Asn Asp Phe Lys Tyr Tyr
                165                 170                 175 ctc agc gat tat aac tac gcg ttt tca att ata gat aat act aca aat        576
Leu Ser Asp Tyr Asn Tyr Ala Phe Ser Ile Ile Asp Asn Thr Thr Asn
                180                 185                 190 gtt ctt gtt gcg ttt ggt ttg tat cgt taa                                606
Val Leu Val Ala Phe Gly Leu Tyr Arg
                195                 200

<210> SEQ ID NO 10
<211> LENGTH: 201
<212> TYPE: PRT
<213> ORGANISM: Autographa californica nucleopolyhedrovirus

<400> SEQUENCE: 10

Met Ala Val Ile Phe Asn Asn Lys Gln Leu Leu Ala Asp Asn Ser Ile
 1               5                  10                  15

Glu Lys Gly Gly Glu Leu Phe Leu Phe Asn Gly Ser Tyr Asn Ile Leu
                20                  25                  30

Glu Ser Tyr Val Asn Pro Val Leu Leu Lys Asn Gly Val Ile Glu Leu
            35                  40                  45

Glu Glu Ala Ala Tyr Tyr Ala Gly Asn Ile Leu Tyr Lys Thr Asp Asp
        50                  55                  60

Pro Lys Phe Ile Asp Tyr Ile Asn Leu Ile Ile Lys Ala Thr His Ser
65                  70                  75                  80

Glu Glu Leu Pro Glu Asn Ser Thr Val Val Asn Tyr Arg Lys Thr Met
                85                  90                  95

Arg Ser Gly Thr Ile His Pro Ile Lys Lys Asp Ile Tyr Ile Tyr Asp
                100                 105                 110

Asn Lys Lys Phe Thr Leu Tyr Asp Arg Tyr Ile Tyr Gly Tyr Asp Asn
            115                 120                 125

Asn Tyr Val Asn Phe Tyr Glu Asp Lys Asn Glu Lys Glu Lys Glu Tyr
        130                 135                 140

Glu Glu Glu Asp Asp Lys Ala Ser Ser Leu Arg Glu Ser Lys Ile Ile
145                 150                 155                 160

Leu Ser Gln Ile Asn Cys Glu Ser Phe Glu Asn Asp Phe Lys Tyr Tyr
                165                 170                 175

Leu Ser Asp Tyr Asn Tyr Ala Phe Ser Ile Ile Asp Asn Thr Thr Asn
                180                 185                 190

Val Leu Val Ala Phe Gly Leu Tyr Arg
                195                 200

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
agcttcctgc aggactagtc ccggcaattc cctgaggt                               38
```

-continued

```
<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ctagacctca gggaattccc gggactagtc ctgcagga                              38
```